US010117744B2

(12) United States Patent
Ratz et al.

(10) Patent No.: US 10,117,744 B2
(45) Date of Patent: Nov. 6, 2018

(54) REPLACEMENT HEART VALVES AND METHODS OF DELIVERY

(71) Applicant: Edwards Lifesciences CardiAQ LLC, Irvine, CA (US)

(72) Inventors: J. Brent Ratz, Winchester, MA (US); Luca Pesce, Huntington Beach, CA (US); Siddharth Vad, Irvine, CA (US); Garrett Dallas Johnson, Costa Mesa, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 15/247,461

(22) Filed: Aug. 25, 2016

(65) Prior Publication Data
US 2017/0056166 A1 Mar. 2, 2017

Related U.S. Application Data

(60) Provisional application No. 62/266,394, filed on Dec. 11, 2015, provisional application No. 62/210,274, filed on Aug. 26, 2015.

(51) Int. Cl.
*A61F 2/06* (2013.01)
*A61F 2/24* (2006.01)

(52) U.S. Cl.
CPC .... *A61F 2/2418* (2013.01); *A61F 2220/0008* (2013.01); *A61F 2230/0013* (2013.01);
(Continued)

(58) Field of Classification Search
CPC ........ A61F 2/24; A61F 2/2409; A61F 2/2412; A61F 2/2418; A61F 2/246;
(Continued)

(56) References Cited

U.S. PATENT DOCUMENTS 3,657,744 A 4/1972 Ersek
3,671,979 A 6/1972 Moulopoulos
(Continued)

FOREIGN PATENT DOCUMENTS

CA 2304325 A1 10/2000
CA 2827556 A1 7/2012
(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
(Continued)

*Primary Examiner* — Brian Dukert
(74) *Attorney, Agent, or Firm* — Knobbe Martens Olson & Bear LLP

(57) ABSTRACT

A valve prosthesis can be configured to be deployed within a native heart valve and prevent axial flow of fluid around an exterior of the prosthesis. The prosthesis can include an expandable frame configured to radially expand and contract for deployment within the native heart valve, a flap assembly positioned around an exterior of the expandable frame, a proximal end of the flap assembly being positioned at or proximate a proximal end of the expandable frame. In some embodiments, the flap assembly can extend outward from the frame and have an expanded configuration configured to create a barrier to fluid flow exterior to the frame when deployed within the native heart valve.

24 Claims, 24 Drawing Sheets

(52) U.S. Cl.
CPC ............... *A61F 2250/0003* (2013.01); *A61F 2250/0069* (2013.01)

(58) Field of Classification Search
CPC ...... A61F 2250/0003; A61F 2250/0069; A61F 2210/0061
See application file for complete search history.

(56) References Cited

U.S. PATENT DOCUMENTS

| | | | |
|---|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | DiMatteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,730,118 B2 | 5/2004 | Spenser et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,203 B2 | 2/2014 | Quadri et al. |

(56) References Cited

U.S. PATENT DOCUMENTS

| | | |
|---|---|---|
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,289,291 B2 | 3/2016 | Gorman, III et al. |
| 9,289,296 B2 | 3/2016 | Braido et al. |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0082094 A1* | 4/2010 | Quadri .................. A61F 2/2412 623/1.26 |

(56) References Cited

U.S. PATENT DOCUMENTS

| | | |
|---|---|---|
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0304200 A1 | 11/2013 | McLean et al. |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0257467 A1 | 9/2014 | Lane et al. |
| 2014/0257475 A1 | 9/2014 | Gross et al. |
| 2014/0277390 A1 | 9/2014 | Ratz et al. |
| 2014/0277402 A1 | 9/2014 | Essinger et al. |
| 2014/0277412 A1 | 9/2014 | Bortlein et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1* | 1/2015 | Para .................. A61F 2/2418 623/1.2 |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1* | 12/2015 | Morriss .................. A61F 2/2418 623/2.11 |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0213473 A1 | 7/2016 | Hacohen et al. |
| 2016/0235529 A1 | 8/2016 | Ma et al. |
| 2016/0310267 A1* | 10/2016 | Zeng .................. A61F 2/2418 |

FOREIGN PATENT DOCUMENTS

| | | |
|---|---|---|
| DE | 102006052564 B3 | 12/2007 |
| EP | 1259194 B1 | 2/2005 |
| EP | 1255510 B1 | 4/2007 |
| EP | 1472996 B1 | 9/2009 |
| EP | 2308425 A1 | 4/2011 |
| EP | 1281375 B1 | 2/2012 |
| EP | 2496182 A1 | 9/2012 |
| EP | 2285317 B1 | 12/2012 |
| EP | 2566416 A1 | 3/2013 |
| EP | 2319458 B1 | 4/2013 |
| EP | 2124826 B1 | 7/2014 |
| EP | 2777616 A1 | 9/2014 |
| EP | 2777617 A1 | 9/2014 |
| EP | 2745805 B1 | 6/2015 |
| EP | 2749254 B1 | 6/2015 |
| EP | 2898858 A1 | 7/2015 |
| EP | 1734903 B1 | 10/2015 |
| EP | 2926766 B1 | 10/2015 |

(56) References Cited

FOREIGN PATENT DOCUMENTS

| | | |
|---|---|---|
| EP | 2985006 A1 | 2/2016 |
| EP | 2815725 B1 | 4/2016 |
| EP | 2237746 B1 | 5/2016 |
| EP | 2815723 B1 | 7/2016 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 0061034 A1 | 10/2000 |
| WO | 03092554 A1 | 11/2003 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009094500 A1 | 7/2009 |
| WO | 2009134701 A2 | 11/2009 |
| WO | 2010008549 A1 | 1/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013059747 A1 | 4/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014022124 A1 | 2/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |
| WO | 2016176144 A2 | 11/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. of 2010.

Int'l. Search Report for PCT/US2016/049045, dated Dec. 5, 2016.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. of 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Spillner, J. et al., "New Sutureless 'Atrial- Mitral-Valve Prosthesis' for Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. of 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

(56) References Cited

OTHER PUBLICATIONS

Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.
Ratz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes his may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve® system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve, " Reviews in Interventional Cardiology, Circ. Cardiovasc. Intervent., 2008;1:74-81, Applicant believes this may be available as early as Aug. of 2008.
Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. of 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first-in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional cardiology, Dec. 30, 2014, p. 3, <http://www.dicardiology.com/article/transcatheter-mitral-valve-replacement-devices-development>.
The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Neovasc corporate presentation, Oct. 2009, available at http://www.neovasc.com/investors/documents/Neovasc-corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.

\* cited by examiner

REPLACEMENT HEART VALVES AND METHODS OF DELIVERY

CROSS-REFERENCE TO RELATED APPLICATIONS

This application claims priority to U.S. Provisional App. No. 62/210,274 filed Aug. 26, 2015, titled REPLACEMENT HEART VALVES AND METHODS OF DELIVERY, and U.S. Provisional App. No. 62/266,394 filed Dec. 11, 2015, titled REPLACEMENT HEART VALVES AND METHODS OF DELIVERY, the entirety of each of which is hereby incorporated herein by reference in its entirety and is to be considered a part of this specification.

BACKGROUND

Field

Certain embodiments disclosed herein relate generally to prostheses for implantation within a lumen or body cavity. In particular, certain embodiments relate to expandable prostheses such as replacement heart valves, such as for the mitral valve.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner. These replacement valves are often intended to at least partially block blood flow. However, a problem occurs when blood flows around the valve on the outside of the prosthesis. For example, in the context of replacement heart valves, paravalvular leakage has proven particularly challenging.

SUMMARY

Embodiments of the present disclosure are directed to a prosthesis, such as but not limited to a replacement heart valve. The valve prosthesis can be deployed within a native heart valve.

In some embodiments, the prosthesis can include an expandable frame having a proximal end, a distal end and a longitudinal axis extending therethrough. In some embodiments, the frame can collapse radially for delivery and to expand radially upon deployment. In some embodiments, the prosthesis can also include a distal anchoring feature extending from the frame. In some embodiments, the distal anchoring feature can be expandable from a collapsed configuration to an expanded configuration. In some embodiments, the prosthesis can also include a valve body positioned within an interior of the expandable frame. In some embodiments, the valve can include a plurality of leaflets. In some embodiments, the leaflets can allow flow in a first direction and prevent flow in a second opposite direction. In some embodiments, the prosthesis can include a flap assembly. In some embodiments, the flap assembly can be positioned around and secured to an exterior of the expandable frame. In some embodiments, the prosthesis can include at least one biasing arm extending radially outward from the frame when the frame is in an expanded configuration. In some embodiments, the at least one biasing arm can be configured to bias the flap assembly radially outward from the longitudinal axis of the frame to provide a space between the flap assembly and the valve body. In some embodiments, fluid flow into the space can cause the flap assembly to move from a first configuration to a second configuration which can create a barrier to fluid flow exterior to the frame when the valve prosthesis is deployed within the native heart valve.

In some embodiments, the at least one biasing arm can include a plurality of biasing arms. In some embodiments, the biasing arm can extend from a middle portion of the frame. In some embodiments, the at least one biasing arm can extend from a distal end of a cell of the frame. In some embodiments, the valve prosthesis can include a strut having a plurality of eyelets, wherein the strut can extend from a distal end of the of the cell from which the at least one biasing arm extends. In some embodiments, the at least one biasing arm can extend proximally and the strut extends distally. In some embodiments, the at least one biasing arm can extend from a proximal end of a cell of the frame. In some embodiments, the at least one biasing arm can extend towards a proximal end of the frame. In some embodiments, the at least one biasing arm can extend towards a distal end of the frame. In some embodiments, the biasing arm can bias the flap assembly radially outwards from an exterior of the frame. In some embodiments, the biasing arm can be positioned within an interior of the flap assembly. In some embodiments, the biasing arm can be positioned along an exterior of the flap assembly.

In some embodiments, an internal volume of the flap assembly in the second configuration can be greater than the volume of the flap assembly in the first configuration. In some embodiments, a distal end of the flap assembly can extend to the distal end of the frame. In some embodiments, a distal end of the flap assembly can include a plurality of tabs, wherein each of the tabs can be attached to a portion of the distal anchoring feature. In some embodiments, a distal end of the flap assembly can be attached to the frame. In some embodiments, a proximal end of the flap assembly can be attached to the proximal end of the frame. In some embodiments, a proximal end of the flap assembly can follow a curvature of the proximal end of the frame. In some embodiments, a proximal end of the flap assembly can extend along an exterior of the proximal end of the frame. In some embodiments, a proximal end of the flap assembly can extend along an interior of the proximal end of the frame. In some embodiments, the prosthesis can also include a proximal anchoring feature extending from the frame. In some embodiments, the proximal anchoring feature can be expandable from a collapsed configuration to an expanded configuration.

In some embodiments, the prostheses can also include a liner extending along an interior of the frame. In some embodiments, the liner can be attached to the leaflets of the valve. In some embodiments, the flap assembly can be attached to the liner.

In some embodiments, the prosthesis can include an expandable frame having a proximal end, a distal end and a longitudinal axis extending therethrough. In some embodiments, the frame can collapse radially for delivery and expand radially upon deployment. In some embodiments, the frame can include a plurality of foreshortening cells and a plurality of struts having one or more eyelet. In some embodiments, the struts can extend distally from the frame and can extend further distally than the foreshortening cells. In some embodiments, the prosthesis can include a distal anchoring feature which can extend from the frame. In some embodiments, the distal anchoring feature can be expandable from a collapsed configuration to an expanded configuration. In some embodiments, the distal anchoring feature can include a plurality of anchors, wherein at least some of the plurality of anchors extend from distal ends of the struts. In some embodiments, the prosthesis can include a valve body positioned within an interior of the expandable frame. In some embodiments, the valve body can include a plurality of leaflets. In some embodiments, the leaflets can allow flow in a first direction and prevent flow in a second opposite direction.

In some embodiments, ends of one or more anchors are not generally aligned axially with ends of other anchors when the frame is in an expanded configuration. In some embodiments, one or more anchors extend further distally than other anchors when the frame is in an expanded configuration.

In some embodiments, the prosthesis can include a proximal anchoring feature extending from the frame. In some embodiments, the proximal anchoring feature can be expandable from a collapsed configuration to an expanded configuration. In some embodiments, the proximal anchoring feature can include a shoulder. In some embodiments, the shoulder can include an end which extends radially inwardly towards the longitudinal axis.

In some embodiments, the prosthesis can include an expandable frame having a proximal end, a distal end and a longitudinal axis extending therethrough. In some embodiments, the frame can collapse radially for delivery and expand radially upon deployment. In some embodiments, the prosthesis can include a proximal anchoring feature extending from the frame. In some embodiments, the proximal anchoring feature can be expandable from a collapsed configuration to an expanded configuration. In some embodiments, the proximal anchoring feature can include a shoulder. In some embodiments, the shoulder can have an end which extends radially inwardly towards the longitudinal axis. In some embodiments, the prosthesis can include a valve body positioned within an interior of the expandable frame. In some embodiments, the valve body can include a plurality of leaflets. In some embodiments, the leaflets can be configured to allow flow in a first direction and prevent flow in a second opposite direction.

In some embodiments, the shoulder can include a first bend in which the shoulder extends radially outwardly from a longitudinal axis of the expandable frame. In some embodiments, the shoulder can include a second bend in which the shoulder extends radially inwardly towards the longitudinal axis.

In some embodiments, the prosthesis can include an expandable frame having a proximal end, a distal end and a longitudinal axis extending therethrough. In some embodiments, the frame can collapse radially for delivery and expand radially upon deployment. In some embodiments, the frame can include a plurality of foreshortening cells sized to be positioned within a patient's native mitral valve annulus when the frame is in an expanded configuration. In some embodiments, the prosthesis can include a proximal anchoring feature. In some embodiments, the proximal anchoring feature can be expandable from a collapsed configuration to an expanded configuration. In some embodiments, the proximal anchoring feature in an expanded configuration can include a shoulder. In some embodiments, the shoulder can be formed at least partially from the plurality of foreshortening cells. In some embodiments, the cells at least partially forming the shoulder can first bend radially outward relative to the longitudinal axis. In some embodiments, the cells at least partially forming the shoulder can then bend radially inward toward the longitudinal axis. In some embodiments, the shoulder can be positionable within the left atrium and have an outer dimension larger than an inner edge of the native mitral valve annulus. In some embodiments, the proximal anchoring feature in an expanded configuration can include a plurality of elongate tips. In some embodiments, the plurality of elongate tips can be located proximal to the shoulder and extend generally proximally. In some embodiments, the prosthesis can include a distal anchoring feature. In some embodiments, the distal anchoring feature can be expandable from a collapsed configuration to an expanded configuration. In some embodiments, the distal anchoring feature in an expanded configuration can include a plurality of anchors having tips. In some embodiments, the tips can be positioned radially outward from an outer surface the frame. In some embodiments, the tips can extend generally proximally to engage tissue on a ventricular side of the native mitral valve annulus. In some embodiments, the prosthesis can include a valve body positioned within an interior of the expandable frame. In some embodiments, the valve body can include a plurality of leaflets. In some embodiments, the plurality of leaflets can allow flow in a proximal-to-distal direction and to prevent flow in a distal-to-proximal direction.

In some embodiments, the plurality of elongate tips can extend parallel to the longitudinal axis. In some embodiments, the plurality of elongate tips can extend radially inwardly. In some embodiments, at least some of the plurality of elongate tips can have enlarged ends for engagement with a delivery device. In some embodiments, each of the plurality of anchors can first extend distally away from the plurality of foreshortening cells and can include one or more bends that cause the tips of the plurality of anchors to extend generally proximally. In some embodiments, some of the plurality of anchors can extend further distally compared to others of the plurality of anchors before bending in a generally proximal direction. In some embodiments, each of the plurality of anchors can have a tip that is located at the same axial location relative to the outer surface of the frame when the distal anchoring feature is in an expanded configuration. In some embodiments, some of the plurality of anchors can extend from struts having a plurality of eyelets. In some embodiments, the struts having a plurality of eyelets can extend distally from corresponding foreshortening cells.

In some embodiments, the frame can include two rows of foreshortening cells. In some embodiments, the prosthesis can include a flap assembly positioned around a portion of the frame. In some embodiments, the flap can have an expanded configuration to create a barrier to fluid flow exterior to the frame when deployed. In some embodiments, the prosthesis can include a plurality of arms extending from the frame. In some embodiments, the plurality of arms can be sized to bias the flap assembly to its expanded configuration.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION

Figure 1:
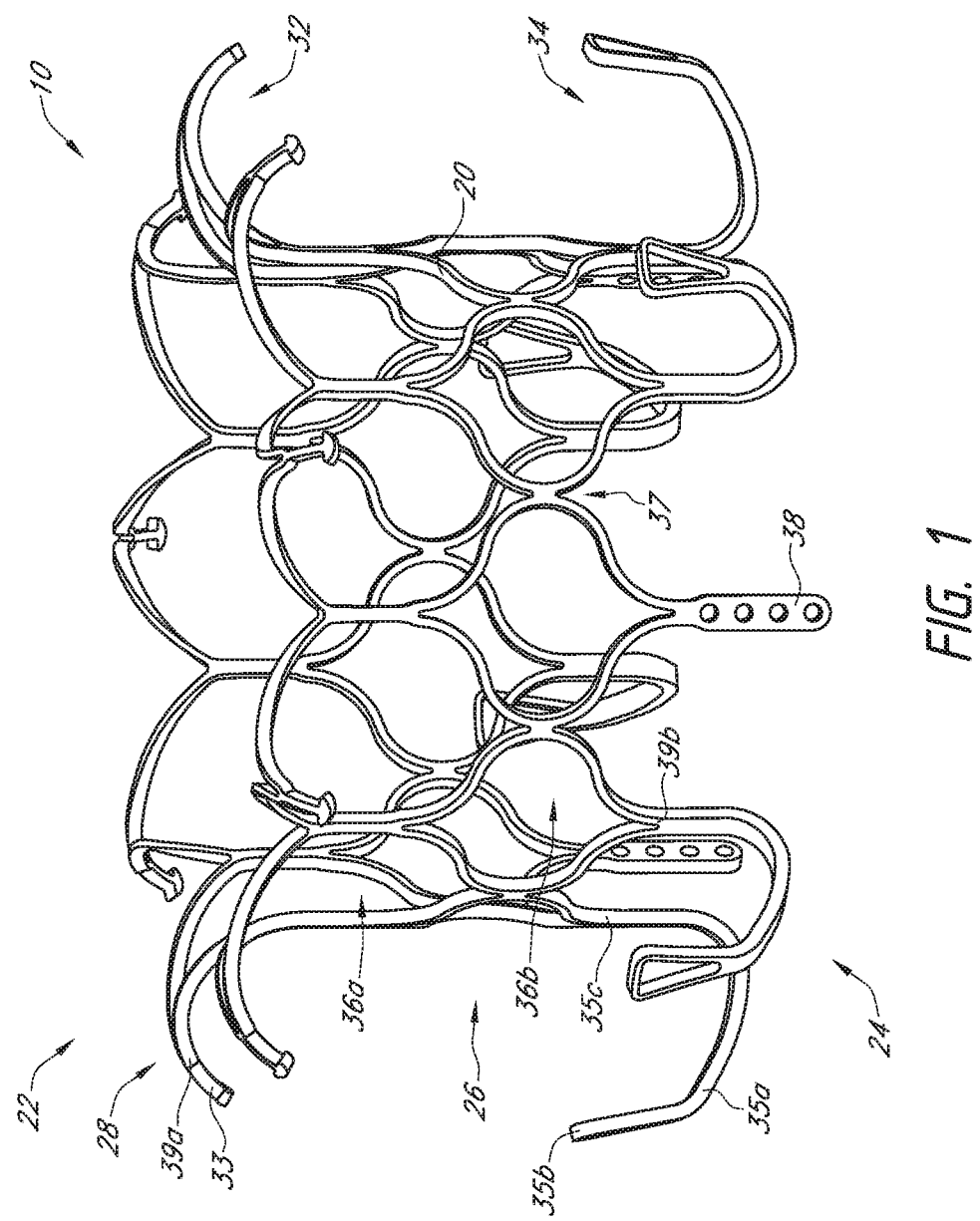
FIG. 1 is a perspective view of an embodiment of a prosthesis.

The present specification and drawings provide aspects and features of the disclosure in the context of several embodiments of prostheses, replacement heart valves, delivery devices and methods that are configured for use in the vasculature of a patient, such as for replacement of natural heart valves in a patient. These embodiments may be discussed in connection with replacing specific valves such as the patient's mitral valve. However, it is to be understood that the features and concepts discussed herein can be applied to replacing other types of valves including, but not limited to, the aortic valve, the pulmonary valve, and the triscupid valve. Moreover, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within a vein, or the like. In addition, particular features of a prosthesis should not be taken as limiting, and features of any one embodiment discussed herein can be combined with features of other embodiments as desired and when appropriate.

Certain terminology may be used in the following description for the purpose of reference only, and thus are not intended to be limiting. For example, terms such as "upper", "lower", "upward", "downward", "above" and "below" refer to directions in the drawings to which reference is made. Terms such as "proximal", "distal", and "side" describe the orientation and/or location of portions of the components or elements within a consistent but arbitrary frame of reference which is made clear by reference to the text and the associated drawings describing the components or elements under discussion. Such terminology may include the words specifically mentioned above, derivatives thereof, and words of similar import. Similarly, the terms "first", "second", and other such numerical terms referring to structures do not imply a sequence or order unless clearly indicated by the context.

In some embodiments, the term "proximal" may refer to the parts of the device and system which are located closer to the operator of the device and system (e.g., the clinician implanting the prosthesis). The term "distal" may refer to the parts of the device and system which are located further from the operator of the device and system (e.g., the clinician implanting the prosthesis).

The embodiment of FIGS. 1-5 illustrate a prosthesis 10 in an expanded configuration which can be configured as replacement heart valve. The prosthesis 10 can be a replacement heart valve having features similar to those disclosed in U.S. Publication Nos. 2014/0277422, 2014/0277427, 2014/0277390, 2015/0328000, the entirety of each of which is hereby incorporated by reference and made a part of this specification. This is inclusive of the entire disclosure and is not in any way limited to the disclosure of the replacement heart valve.

Figure 2:
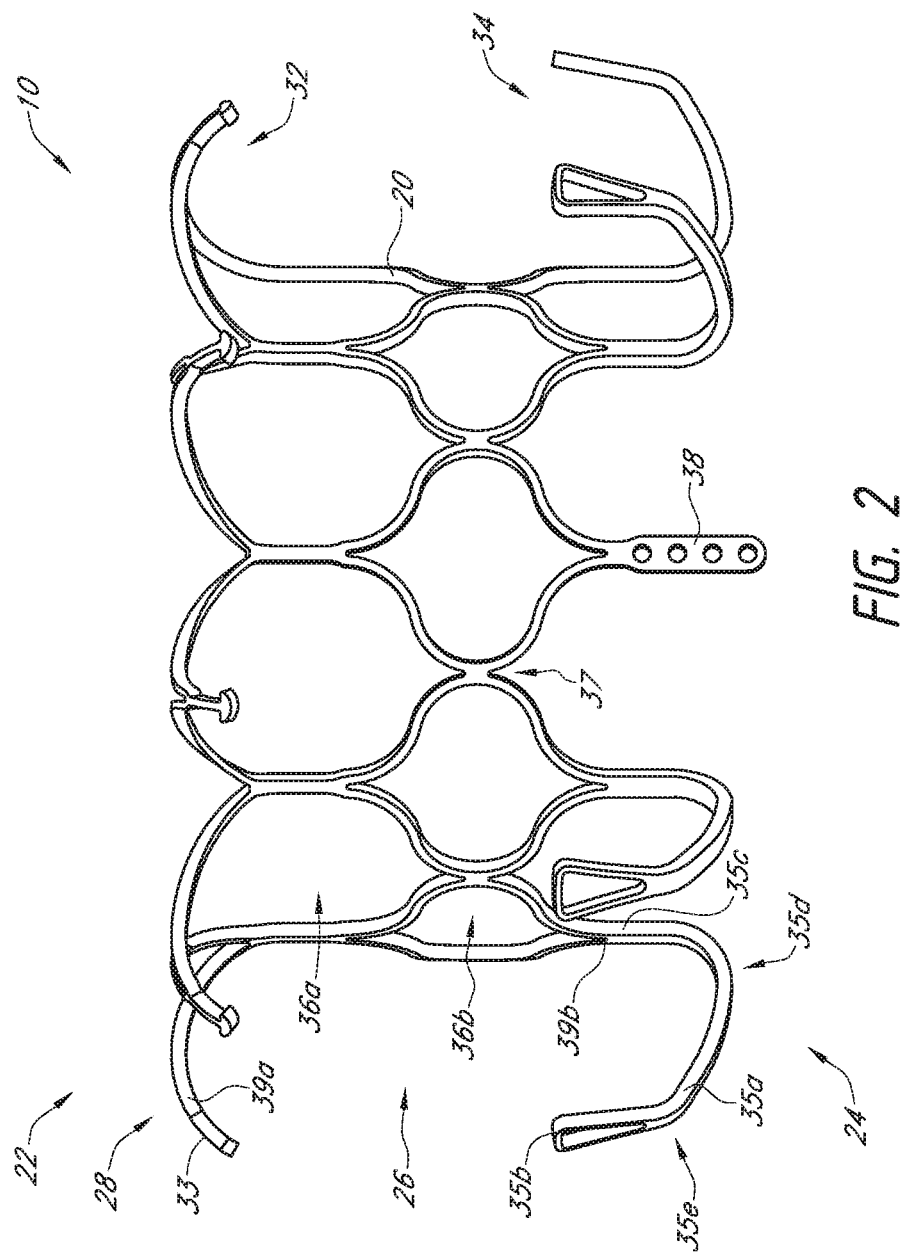
FIG. 2 is a side view of the prosthesis of FIG. 1, illustrating a half of the prosthesis.

With reference first to the embodiment of FIGS. 1 and 2, the prosthesis 10 can include a frame 20 that can be self-expanding or balloon expandable. The frame 20 can have a first end 22, a second end 24, a middle or intermediate portion 26, a first anchoring feature 32 and a second anchoring feature 34. In some embodiments, the frame 20 may be oriented such that the first end 22 is a proximal end, the second end 24 is a distal end, the first anchoring feature 32 is a proximal anchoring feature and the second anchoring portion 34 is a distal anchoring feature. One or both anchoring features 32, 34 can contact or engage a native valve annulus, such as the native mitral valve annulus, tissue beyond the native valve annulus, native leaflets, and/or other tissue at or around the implantation location. While the anchoring features 32, 34 have been illustrated as extending from the first and second ends 22, 24 of the frame 20 respectively, it should be understood that the anchoring features 32, 34 can be positioned along any other portion of the frame 20 as desired. Moreover, while two anchoring features 32, 34 have been included in the illustrated embodiment, it is contemplated that fewer or greater sets of anchoring features can be utilized.

With continued reference to the embodiment of FIGS. 1 and 2, the frame 20 can include a number of struts with at least some of the struts forming cells 36a and 36b. The struts may be arranged so that they are parallel or generally or substantially parallel to a longitudinal axis of the frame 20. The longitudinal axis of the frame 20 may be defined as the central axis that extends through the center of the frame 20 between the first and second ends 22, 24 of the frame 20.

One or more struts 38 can include eyelets. As illustrated, a plurality of eyelets are located along the strut 38 and extend along a single row. As will be described below, the eyelets may be used to attach features such as the valve 40, liner 50, and/or flap or sail assembly 60 to the frame 20. As also shown in the illustrated embodiment, the struts 38 having eyelets can extend from a distal-most end of the cells 36b in a direction parallel with the longitudinal axis of the frame, although it is also contemplated that the struts 38 can extend from other portions of the frame 20 such as the interconnecting regions 37 between the cells 36a, 36b, the proximal-most end of the cells 36a, 36b, or any other portion as desired such as apices, junctions, other parts of struts, etc.

Any number of configurations of struts can be used, such as the rings of undulating struts shown forming ellipses, ovals, rounded polygons, and teardrops, but also chevrons, diamonds, curves, and various other shapes. The illustrated embodiment of FIGS. 1 and 2 includes two rows of cells 36a, 36b. The two rows of cells 36a, 36b can include an interconnecting region 37 between each cell 36a, 36b. While the present embodiment of FIGS. 1 and 2 illustrate two adjacent cells positioned relatively close together, the interconnecting region 37 can include a laterally extending structure between two adjacent cells 36a, 36b to increase separation distance. This can allow the cells 36a, 36b to more easily deform thereby facilitating the transition from the collapsed configuration to the expanded configuration.

With continued reference to the embodiment of FIGS. 1 and 2, there can be two rows of nine cells 36a, 36b with the first row of cells 36a positioned closer to the first end 22 of the frame 20 and the second row positioned closer to the second end 24 of the frame 20. The cells 36b in the second row can share struts from the cells 36a of the first row. As shown in the illustrated embodiment, the cells 36b in the second row can have a different shape from the cells 36a of the first row. When in the expanded configuration, cells 36a can have two longitudinally extending sides with the lower end having a pointed onion-shape. The upper end, which can form part of the first anchoring feature 32 can have a pointed onion-shape similar to the lower end. When in the expanded configuration, cells 36b can have a generally elliptical shape with pointed, outwardly extending ends along the upper and lower sections such that cells 36b resemble an onion. The cells 36c can be formed between two struts having a compressed "bell curve" shape. Cells 36a can be larger than cells 36b. In other embodiments, the cells 36b of the second row can have the same shape as the cells 36a of the first row. While each of the cells 36a, 36b are shown having the same shape as other cells 36a, 36b, of the same row, it is contemplated that the shapes of cells 36a, 36b, within a row can differ.

As shown in the illustrated embodiment, a portion of the frame 20, such as the first row of cells 36a, can extend radially outward from the longitudinal axis of the frame 20. In this manner, the cells 36a can create a flared or shoulder portion 28 of the frame 20. This flared or shoulder portion 28 can form part of the first anchoring feature 32 of the prosthesis 10. As shown in the illustrated embodiment, a portion of the frame 20, such as the cells 36a, can extend radially outward via a bend beginning at or proximate the ends the struts forming the longitudinally extending sides of cells 36a. The radius of curvature of this bend can be relatively constant throughout the length of the bend or can differ along the length of the bend. For example, the radius of curvature may increase from the beginning of the bend towards the end of the bend, such as ends 39a of cells 36a, or may decrease from the beginning of the bend towards the ends of the bend, such as ends 39a of cells 36a. Moreover, the ends 39a of cells 36a can extend radially outward from the longitudinal axis of the frame 20 in a direction generally perpendicular to the longitudinal axis. In some embodiments, the frame 20 can include a second bend, after the first bend, which extends the frame in an different direction from the first bend. For example, the second bend can cause a portion of the frame 20, such as cells 36a, to curve radially inward towards the longitudinal axis of the frame 20. In some embodiments, the ends 39a of cells 36a can extend in a direction generally parallel to the longitudinal axis or further radially inward. A greater number of bends may also be incorporated.

As shown in the illustrated embodiment, the ends 39a of cells 36a extend in a direction which forms an acute angle relative to a perpendicular line passing through the longitudinal axis of the frame 20. For example, the angle can be between about 0 degrees and about 30 degrees, between about 5 degrees and about 25 degrees, between about 10 degrees and about 20 degrees, any sub-range within these ranges, or any other angle as desired. The ends 39a of cells 36a can be at or proximate the upper-most portion of the frame 20. The ends 39a of the cells 36a can also extend towards the second end 24 of the frame 20. The second row of cells 36b can extend in a direction generally parallel to the longitudinal axis of the frame 20. As shown in the illustrated embodiment, the ends 39b of the cells 36b can extend in a direction generally parallel to the longitudinal axis of the frame 20.

In some embodiments, the bend formed along a portion of the frame 20, such as cells 36a, can generally form an arc with an angle between about 90 degrees to about 180 degrees such that, at the end of the bend, the frame 20 extends in a direction radially outward from a longitudinal axis of the frame 20 and towards the second end 24 of the frame 20. For example, as shown in the illustrated embodiment, the arc can have an angle of about 110 degrees. In some embodiments, the bend of cells 36a can form an arc with an angle between about 0 degrees to about 90 degrees such that, at the end of the bend, the frame 20 extends in a direction radially outward from a longitudinal axis of the frame 20 and upwards. In some embodiments, the bend of cells 36a can form an arc with an angle between about 180 degrees to about 270 degrees such that, at the end of the bend, the frame 20 extends in a direction radially inward towards a longitudinal axis of the frame 20 and towards a second end 24 of the frame 20. In some embodiments, the bend of cells 36a can form an arc with an angle between about 270 degrees to about 360 degrees such that, at the end of the bend, the frame 20 extends in a direction radially inward towards a longitudinal axis of the frame 20 and upwards.

As noted above, the radius of curvature of the arc may be constant such that the bend forms a circular arc or may differ along the length of the bend. Moreover, as noted above, the frame 20 can incorporate additional bends after the initial bend. Such bends can incorporate the structural features described above. For example, in some embodiments, the frame 20 can include a first bend forming an arc with an angle between about 60 degrees to about 100 degrees and a second bend, in an opposite direction, which forms an arc with an angle between about 90 degrees to about 180 degrees.

Figure 3:
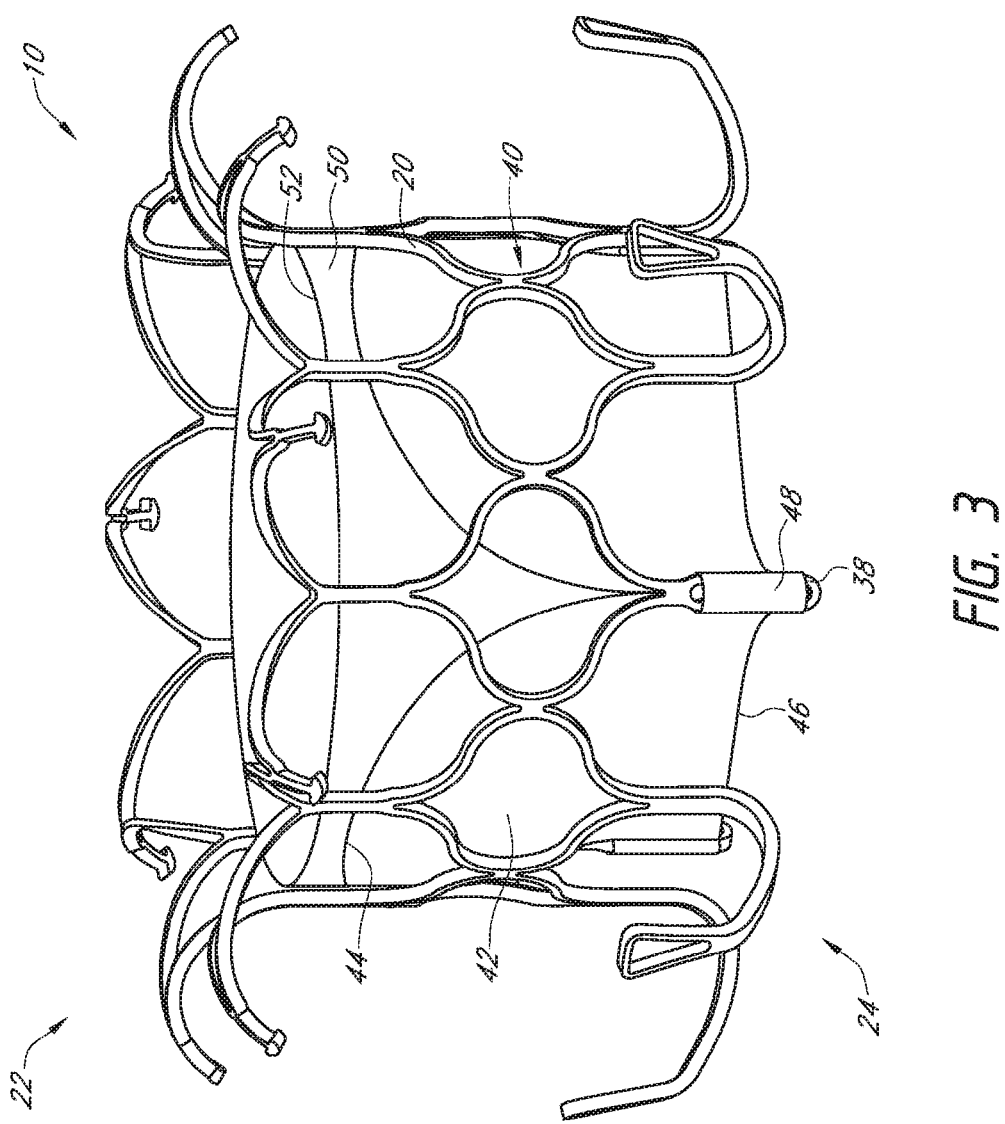
FIG. 3 is a perspective view of the prosthesis of FIG. 1, with embodiments of a valve and a liner attached thereto.

The cells 36b can be generally parallel with the longitudinal axis of the frame 20. In this manner, the cells 36b can create a cylindrical portion of the frame 20. In some embodiments, the valve 40 (as shown in FIG. 3) can be positioned within the cylindrical portion. Although the frame 20 has been described as having two rows of nine cells 36a, 36b each, any number of rows can be used and any number of cells may be contained in the rows. In some embodiments, the number of cells can correspond to the number of anchors forming the first anchoring feature 32, the number of anchors forming the second anchoring feature 34 and/or struts having eyelets 38.

Cells 36a, 36b can allow the frame 20 to foreshorten. Foreshortening of the frame 20 can be used to secure the prosthesis to intralumenal tissue in a body cavity, for example tissue at or adjacent a native valve, such as a native valve annulus and/or leaflets. Opposing anchoring features 32, 34 can be constructed on the frame 20 so that portions of the anchoring features 32, 34, such as the flared or shoulder portion 28, tips 33 extending from ends 39a, and/or tips 35b extending from anchors 35a, move closer together as the frame 20 foreshortens. As one example, this can allow the anchoring features 32, 34 to close in on opposite sides of the native mitral annulus to thereby secure the prosthesis at the mitral valve. In some embodiments, the anchoring features 32, 34 can be positioned such that the anchoring features 32, 34 do not contact the native mitral annulus at the same time. For example, in some situations, the anchoring feature 34 may contact the native mitral annulus while the anchoring feature 32 does not contact the native mitral annulus. In some embodiments, the anchoring features 32, 34 can be positioned such that the anchoring features 32, 34 grasp opposite side of the native mitral annulus.

With continued reference to the embodiment of FIGS. 1 and 2, the frame 20 can have a cylindrical or slightly cylindrical shape when in the expanded configuration. The cylindrical shape can correspond to the cells 36b. The middle portion 26 of the frame 20 can be substantially similar in shape and size as the second end 24 of the frame 20. The first end 22 can have a diameter which is greater than the diameter of the middle portion 26 of the frame 20 and/or the second end 24 of the frame 20. As noted above, the frame 20 can include an outwardly flared portion or shoulder portion 28 at or adjacent the first end 22 of the frame corresponding to the cells 36a. As will be described in further detail below, the flared or shoulder portion 28 can facilitate blood flow through the prosthesis 10 from the first end 22 of the frame 20 to the second end 24 of the frame 20.

The second end 22 of the frame 20 can have a diameter which is the same as or similar to that of the middle portion 26 of the frame 20 although it is contemplated that the second end 24 can have a diameter which is greater than that of the middle portion 26. For example, the second end 24 may include a flared or shoulder portion similar to that of the first end 22. In some embodiments, the middle portion 26 can have a diameter which is greater than the diameter of one or both of the first and second ends 22, 24 of the frame 20.

The diameter of the middle portion 26 of the frame 20 can be in the range of about 20 mm to about 40 mm when expanded, in the range of about 25 mm to about 35 mm when expanded, in the range of about 28 mm to about 32 mm when expanded, any other sub-range within these ranges when expanded, or any other diameter when expanded as desired. As shown in the illustrated embodiment, the diameter of the middle portion 26 of the frame 20 can be about 30 mm when expanded.

The diameter of the middle portion 26 of the frame 20 may be chosen such that the middle portion 26 of the frame 20 is adequately spaced from the body cavity when the frame 20 is positioned within the body cavity. For example, in embodiments where the middle portion 26 of the frame 20 is positioned within the native mitral valve, the middle portion 26 may have a diameter which is less than the diameter of the native mitral valve annulus. In situations where the native mitral valve annulus is about 40 mm in diameter, the diameter of the middle portion 26 can be about 30 mm. Accordingly, the diameter of the middle portion 26 may be about 75% of the diameter of the native mitral valve annulus. In some embodiments, the diameter of the middle portion 26 may be between about 40% to about 90% of the diameter of the native valve annulus, between about 60% to about 85%, of the diameter of the native valve annulus, between about 70% to about 80% of the diameter of the native valve annulus, any other sub-range between these ranges, or any other percentage as desired.

In other embodiments, the diameter of the middle portion 26 of the frame 20 may be chosen such that the middle portion 26 of the frame 20 contacts the body cavity. For example, in embodiments where the middle portion 26 of the frame 20 is positioned within the native mitral valve, the middle portion 26 may have a diameter which is about equal to the diameter of the native mitral valve annulus.

The frame 20 can be made of many different materials, but is preferably made from metal. In some embodiments, the frame 20 can be made from a shape memory material, such as nitinol. A wire frame or a metal tube can be used to make the frame. The wire frame of a metal tube can be cut or etched to remove all but the desired metal skeleton. In some embodiments a metal tube is laser cut in a repeating pattern to form the frame 20. The flat pattern can be cut from a metal tube and then the tube can be bent and expanded to the shape shown in FIGS. 1 and 2. The frame 20 can further be expanded and/or compressed and/or otherwise worked to have the desired shape or shapes, such as for introduction and implantation. Although the frame 20 has been described and illustrated as having a circular cross-section, it is contemplated to form all or a portion of the frame 20 into a non-circular cross-section such as, but not limited to, a D-shape, an oval or an otherwise ovoid cross-sectional shape.

With continued reference to the embodiment of FIGS. 1 and 2, as noted above, first anchoring feature 32 can include a flared or shoulder portion 28 of the frame and can include ends 39a of cells 36a. Ends 39a of cells 36a can form a plurality of anchors in the form of free apices which can be used to facilitate anchoring or stabilization of the frame 20 within the body cavity. The first anchoring feature 32 can also include one or more elongate tips 33. The elongate tips 33 can extend from ends 39a of one or more cells 36a forming part of the anchoring feature 32. The second anchoring feature 34 can include one or more individual anchors 35a having tips or ends 35b.

Each of the anchoring features 32, 34 can be positioned or extend generally radially outwardly from the frame 20, such as the middle portion 26 so that the ends 39a of cells 36a, elongate tips 33, and tips or ends 35b of anchors 35a are generally spaced away or radially outward from the rest of the frame 20. The anchors 35a can include a base 35c located on a side opposite the tips or ends 35b. The base 35c can be for example where the anchors 35a begins to extend from or away from the cells 36b.

As shown in the illustrated embodiment, at least some of the anchoring features, such as anchoring features 32, 34, can extend to a radial distance from an exterior surface of the middle portion 26 of the frame 20 that is about 130% or more of the expanded diameter of the frame 20. For example, in some embodiments the middle portion 26 of the frame 20 can have a radius of approximately 15 mm from a longitudinal axis of the frame 20 and one or both anchoring features 32, 34 can extend to a radial distance of approximately 20 mm from the longitudinal axis of the frame 20. This can be particularly advantageous when placed in an annulus of a native valve, such as the annulus of a native mitral valve, which has an effective radius of approximately 20 mm.

In some embodiments, all of the anchors of the first anchoring feature 32, such as ends 39a and/or elongate tips 33, and/or all of the anchors of the second anchoring feature 34, such as anchors 35a, extend at least to this radial distance. In other embodiments, fewer than all of the anchors of the first anchoring feature 32 and/or all of the anchors of the second anchoring feature 34 extend to this radial distance. Other radial distances are also contemplated. In some embodiments, the radial distance of ends, such as tips or ends 33, 35b, 39a of the anchors from a central longitudinal axis passing through the middle of the frame 20 may be about 150% or more, about 180% or more, about 200% or more, about 220% or more, or about 250% or more of the radius of the middle portion 26 of the frame 20 when the frame 20 and the anchors are in expanded configurations. For example, if the radius of the middle portion 26 of the frame 20 is 15 mm and an anchor end is spaced 5 mm from the exterior of the middle portion 26 of the frame 20, the anchor extends 20 mm from the central longitudinal axis of the frame 20, and is 133.33% of the radius of the frame 20.

The outermost tip diameter may be greater than the frame diameter as described above and may be in the range of about 35 mm to about 55 mm when expanded, in the range of about 40 mm to about 50 mm when expanded, in the range of about 40 mm to about 45 mm when expanded, any sub-range within these ranges when expanded, or any other diameter as desired.

The cylindrical shape of the frame 20, in combination with the anchoring features 32, 34, can advantageously allow the frame 20 to float within a native valve while the anchors engage a native valve annulus or other body cavity and spacing the inlet and outlet of the frame 20 away from the heart or vessel wall. This can help reduce undesired contact between the frame 20 of the prosthesis 10 and the heart or vessel, such as the ventricular wall of the heart or the native valve annulus as described above.

With continued reference to the embodiment of FIGS. 1 and 2, the first anchoring feature 32 and the second anchoring feature 34 can extend radially outward from the longitudinal axis of the frame 20 to about the same radial dimension. However, in other embodiments (not shown), the second anchoring feature 34 can be positioned to be not as far radially outward as the first anchoring feature 32, and the tips 35b of the anchors 35a may be positioned radially inward of the tips 33 or ends 39a of the first anchoring feature 32. Such a configuration may be advantageous in positioning and securing the prosthesis in a mitral valve or other body location. In some embodiments, the tips 33 or ends 39a of the first anchoring feature 32 can be positioned further radially outward from the frame 20 than the ends of tips 35b of the anchors 35a when the frame 20 and the anchoring features 32, 34 are in an expanded configuration. In further embodiments, some of the anchors of the first anchoring feature 32 (and/or second anchoring feature 34) may extend to a first radial distance, and other anchors of the first anchoring feature 32 (and/or second anchoring feature 34) may extend to a second radial distance, where the first radial distance is greater than the second radial distance.

With continued reference to the embodiment of FIGS. 1 and 2, the anchors of the second anchoring feature 34 can be circumferentially aligned with respect to the anchors of the first anchoring feature 32. In other embodiments (not shown), the anchors of the second anchoring feature 34 can be circumferentially staggered meaning that the tips or ends 33, 39a of the first anchoring feature 32 are not aligned, and are circumferentially in between the tips or ends 35b of the anchors 35a of the second anchoring feature 34.

It will be understood that the anchoring features 32, 34 can have various other configurations. In some embodiments, individual anchors can extend radially outwardly from the frame at an anchor base and terminate at an anchor tip. The individual anchors can be connected to the frame at one of many different locations including apices, junctions, other parts of struts, etc. For example, as shown in the embodiment of FIGS. 1 and 2, the anchors 35a can extend from an end of the cells 36b although it is also contemplated that the anchors 35a can extend from other portions of the frame 20, such as the interconnecting regions 37 between cells 36a, 36b, the proximal-most end of the cells 36a, 36b, or any other portion as desired.

The anchors forming the anchoring features 32, 34 can comprise first, second, third, or more spaced apart bending stages along the length of each anchor. As shown in the illustrated embodiment, the anchors 35a can extend downwardly from the frame 20 in a direction generally parallel to a longitudinal axis of the frame 20. The anchors 35a include a first bending stage 35d in which the anchors 35a extend radially outward from a longitudinal axis of the frame 20 and towards a first end 22 of the frame 20 and a second bending stage 35e in which the anchors 35a further extend towards the first end 22 of the frame 20 in a direction generally parallel with the longitudinal axis of the frame 20. As shown in the illustrated embodiment, the anchors 35a include a straight segment between the first bending stage 35d and the second bending stage 35e. The straight segment is at roughly a 45 degree angle relative to the longitudinal axis of the frame 20. It is contemplated that the straight segment can be at an acute angle relative to the longitudinal axis of the frame 20. It is also contemplated that the straight segment can be at an angle greater than 45 degrees. In some embodiments, the angle can be between about 10 degrees to about 70 degrees, between about 20 degrees to about 60 degrees, between about 30 degrees to about 50 degrees, any subrange within these ranges, or any other angle as desired. In some embodiments, the anchors 35a may extend generally perpendicular to the longitudinal axis of the frame 20. The anchors can also extend either distally or proximally before and/or after one or more of the bending stages. A portion of the anchor may extend with the frame before or after any bending stages. As shown, the anchors 35a can include loops as described above, having a curved or arcuate atraumatic tip to minimize damage to body tissue. Ends of the first anchoring feature 32 can also comprise loops. Further details that may be incorporated and/or interchanged with the features described herein are disclosed in U.S. Publication Nos. 2014/0277422, 2014/0277427, 2014/0277390, 2015/0328000, which have been incorporated by reference herein.

With continued reference to the embodiment of FIG. 1, the elongate tips 33 can extend from an end 39a of the cells 36a. The elongate tips 33 can be curved and follow the general curvature of the cell 36a. For example, as shown in the illustrated embodiment, the elongate tips 33 continue the curve of the cells 36a. The radius of curvature of the elongate tips 33 can be relatively constant throughout the length of the tip 33 or can differ along the length of the tip 33. For example, the radius may increase from the beginning of the tip 33 towards the end of the tip 33 or may decrease from the beginning of the tip 33 towards the end of the tip 33. In some embodiments, the elongate tips 33 can be relatively straight. In some embodiments, the elongate tips 33 can be curved in a different direction from the ends 39a of cells 36a.

The elongate tips 33 can extend in a direction which forms an acute angle relative to a perpendicular line passing through the longitudinal axis of the frame 20. For example, the angle can be between about 0 degrees and about 60 degrees, between about 15 degrees and about 50 degrees, between about 30 degrees and about 45 degrees, any subrange within these ranges, or any other angle as desired.

As shown in the illustrated embodiment, the prosthesis 10 can have a first anchoring feature 32 with nine anchors, a second anchoring feature 34 with six anchors 35a, and struts 38 having eyelets positioned between every two anchors 35a. The struts 38 having eyelets can be circumferentially aligned with ends 39a and/or elongate tips 33. The number of struts 38 having eyelets can correspond to the total number of commissures of the valve 40. While the struts 38 of the illustrated embodiment extend below a bottom-most portion of the second anchoring feature 34, the struts 38 can extend such that they are generally aligned or proximate a bottom-most portion of the second anchoring feature 34 or above a bottom-most portion of the second anchoring feature 34. In some embodiments, the struts 38 may extend even further below a bottom-most portion of the second anchoring feature 34. The additional spacing between the anchors 35a can facilitate compression of the frame 20 into a smaller form factor thereby allowing the frame 20 to fit within a smaller delivery device. Any number of anchors can be included in first and second anchoring features 32, 34. In other embodiments, instead of a 3:2 correspondence between anchors, other ratios, such as a 1:1 or a 3:1 correspondence between the anchors, are possible. In some embodiments, the struts 38 having eyelets can be positioned between every other anchor 35a. Moreover, such struts 38 can be positioned between anchors of the first anchoring feature 32.

The tips or ends 33, 35b, 39a as described above can advantageously provide atraumatic surfaces that may be used to grasp intralumenal tissue without causing unnecessary or undesired trauma to tissue. For example, the tips or ends 33, 35b, 39a can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the frame 20 is deployed in-situ and the anchoring features 32, 34 expand away from the frame 20, the movement of each loop from a delivered position to a deployed position avoids getting caught on the papillary muscles. As shown in the illustrated embodiment, second anchoring feature 34 include anchors 35a having looped ends with a flattened or rounded top surface. As shown, the ends of tips 33 can be enlarged relative to other portions of the tips 33. For example, the ends of tips 33 can have a generally "mushroom" shape. Tips 33 can be used to engage a locking mechanism of a delivery system for the prosthesis.

In some embodiments (not shown), some of anchors of the first and/or second anchoring features 32, 34 may have different lengths. For example, in some embodiments, one or more of the anchors of the second anchoring feature 34 may be a first length and one or more anchors of the second anchoring feature 34 may be a second length. The second length may be longer than the first length. When used in conjunction with certain delivery systems such as those described in U.S. Publication No. 2015/0238315 and U.S. Application No. 62/210,165 entitled DELIVERY SYSTEM FOR REPLACEMENT MITRAL VALVE AND METHODS OF USE, filed Aug. 26, 2015, the unequal lengths can allow the anchors of the second anchoring feature 34 to be deployed or flipped sequentially. For example, the anchors having a first length can be deployed or flipped first with the anchors having a second length being deployed or flipped second. This can allow some of the anchors to be deployed to confirm positioning of the prosthesis 10 relative to the body cavity prior to deploying additional anchors. This can also apply to anchors of the first anchoring feature 32. For example, in some embodiments, elongate tips 33 can have different lengths. U.S. Publication No. 2015/0238315 and U.S. Application No. 62/210,165, filed Aug. 26, 2015 is hereby incorporated by reference in its entirety and made a part of this specification. U.S. Application No. 62/210,165, filed Aug. 26, 2015, is also included as an Appendix which should be considered a part of this specification.

Because of the dimensions of the anchoring features 32, 34 relative to the size of the frame 20, the frame 20 itself may be made relatively smaller, which also helps facilitate a lower profile for the prosthesis helpful for delivery and implantation. Moreover, having a prosthesis 10 that can "float" within a native annulus may be usable for a wider variety of patient anatomies, as one or a fewer number of radial sizes of the frames can be used to fit a greater number of patients. In such embodiments, because the anchoring features 32, 34 are configured to extend further from the frame 20, these prostheses 10 are still able to securely grasp native tissue as the anchors can expand to different diameters depending on how they are constrained with a body cavity. In the context of a replacement heart valve, the frame (and the associated valve) may have the same size across multiple patient sizes, and the anchors can either be configured to expand to different diameters, or different anchor arrangements may be used for different frames.

With reference next to the embodiment of FIG. 3, the prosthesis 10 can include a valve 40. The valve 40 can be positioned within the frame 20 and can be a replacement heart valve which includes a plurality of valve leaflets 42. The valve leaflets 42 can include a first edge 44, second edge 46, and tabs 48 for attaching the valve leaflets 42 to struts 38 of the frame 20 such as the struts having eyelets 38 (as shown in FIG. 1). The second edge 46 can be a freely moving edge which can allow the valve 40 to open and close. As shown in the illustrated embodiment, the second edge 46 can extend below a bottom-most portion of the second anchoring feature 34 although it is contemplated that the second edge 46 can be positioned at or proximate the bottom-most portion of the second anchoring feature 34 and/or may be positioned above the bottom-most portion of the second anchoring feature 34.

The plurality of valve leaflets 42 can function in a manner similar to the native mitral valve, or to any other valves in the vascular system as desired. The plurality of valve leaflets 42 can open in a first position and then engage one another to close the valve in a second position. The plurality of valve leaflets 42 can be made to function as a one way valve such that flow in one direction opens the valve and flow in a second direction opposite the first direction closes the valve. For example, as shown in the illustrated embodiment, the valve 40 can open allow blood to flow through the valve 40 in a direction from the first end 22 to the second end 24 (e.g., from a proximal end to a distal end). The valve 40 can close to inhibit blood flow through the valve 40 in a direction from the second end 24 to the first end 22 (e.g., from a distal end to a proximal end). The valve 40 can be constructed so as to open naturally with the beating of the heart. For example, the plurality of valve leaflets 42 can open during diastole and close during systole. The valve 40 can replace a damaged or diseased native heart valve such as a diseased native mitral valve.

With continued reference to the embodiment of FIG. 3, the valve 40 can include a liner 50. The liner 50 can be used to assist with fluid flow through and/or around the valve prosthesis 10, such as through and around the frame 20 and the valve leaflets 42. The liner 50 can surround at least a portion of the valve leaflets 42 and be connected to one or more of the valve leaflets 42. For example, as shown in the illustrated embodiment, the one or more valve leaflets 42 can be attached to the liner 50 along the first edge 44 of the valve leaflets 42.

As shown in the illustrated embodiment, the liner 50 can be positioned within the interior of the frame 20 and can form an inner wall of the prosthesis 10. For example, the liner 50 can be positioned such that the liner 50 is radially inward, relative to the longitudinal axis of the frame 20, from the struts of the frame 20. In this manner, the fluid pathway towards the valve leaflets 42 can be relatively smooth. It is also contemplated that the liner 50 can at least be partially positioned along an exterior of the frame 20 such that at least a portion of the liner 50 is radially outward, relative to the longitudinal axis of the frame 20, from struts of the frame 20. As shown in the illustrated embodiment, the liner 50 can be positioned along an inlet side of the prosthesis 10. The liner 50 can extend from the first edge 44 of the valve leaflets 42 towards the first end 22 of the frame 20. The liner 50 can also extend below the first edge 44 of the valve leaflet 42 towards the second end 24 of the frame 20. The liner 50 can also be made to move with foreshortening portions of the frame 20.

The liner 50 can extend the entire length of the frame 20 or it can extend along only part of the length of the frame 20 as shown. In some embodiments, the ends of the valve leaflets 42 can coincide with ends of the liner 50. In addition, one or more of the ends of the frame 20 can coincide with the ends of the liner 50. As shown in the illustrated embodiment, an end 52 of the liner 50 can be positioned between the first end 22 of the frame 20 and the valve leaflets 42. In some embodiments, the end 52 of the liner 50 can extend to the first end 22 of the frame 20 and can also extend over the first end 22. For example, the liner 50 can extend at least partially over the first anchoring feature 32.

Other shapes and configurations can also be used for the valve 40. In some embodiments, the liner 50 may extend along the length of the leaflets, but is not connected to them. In the illustrated embodiment, the liner 50 is attached to the frame 20 and the leaflets 42 are attached to the liner 50. The valve leaflets 42 can also be attached to the frame 20. The liner 50 and/or the valve leaflets 42 can be attached to the frame 20 or to each other using any mechanism or technique as desired such as, but not limited to, mechanical fasteners, such as sutures, staples, screws, rivets, and any other type of mechanical fastener as desired, chemical fasteners such as adhesives and any other type of chemical fastener as desired, fastening techniques such as welding, sintering, and any other type of fastening technique as desired, and/or a combination of such fasteners and techniques.

The liner 50 can be constructed in multiple different ways. The liner 50 can be made a layer of resilient material, such as such as knit polyester (e.g., polyethylene terephthalate (PET)) or any other biocompatible material such as those which are wholly or substantially fluid impermeable, flexible, stretchable, deformable, and/or resilient. In some embodiments, the liner 50 can be made from a material that is more flexible than the valve leaflet material. The distal and/or proximal end, such as end 52, of the liner 50 can be straight, curved, or have any other desired configuration. For example, as shown in the embodiment of FIG. 3, the liner 50 can have a straight edge forming the end 52. In other embodiments, the end 52 can be patterned to generally correspond to the undulations at one end of the frame 20. The liner 50 can be formed of one piece or multiple pieces. For example, the liner 50 attached to the valve leaflets 42 can be one piece and one or more anchors, such as first anchoring feature 32, can be covered by a separate piece of material of the liner 50. It is to be understood that other configurations of the liner 50 can also be employed. For example, anchors of the first anchoring feature 32 may be covered as noted above, or only a portion may be covered.

In another embodiment of the liner 50, the end can extend past the frame 20 and can be wrapped around it. Thus, the liner 50 can extend from the inside of the frame 20 to the outside of the frame 20. The liner 50 can extend completely around the frame 20 for ¼, ⅓, ½, or more of the length of frame 20.

Figure 4:
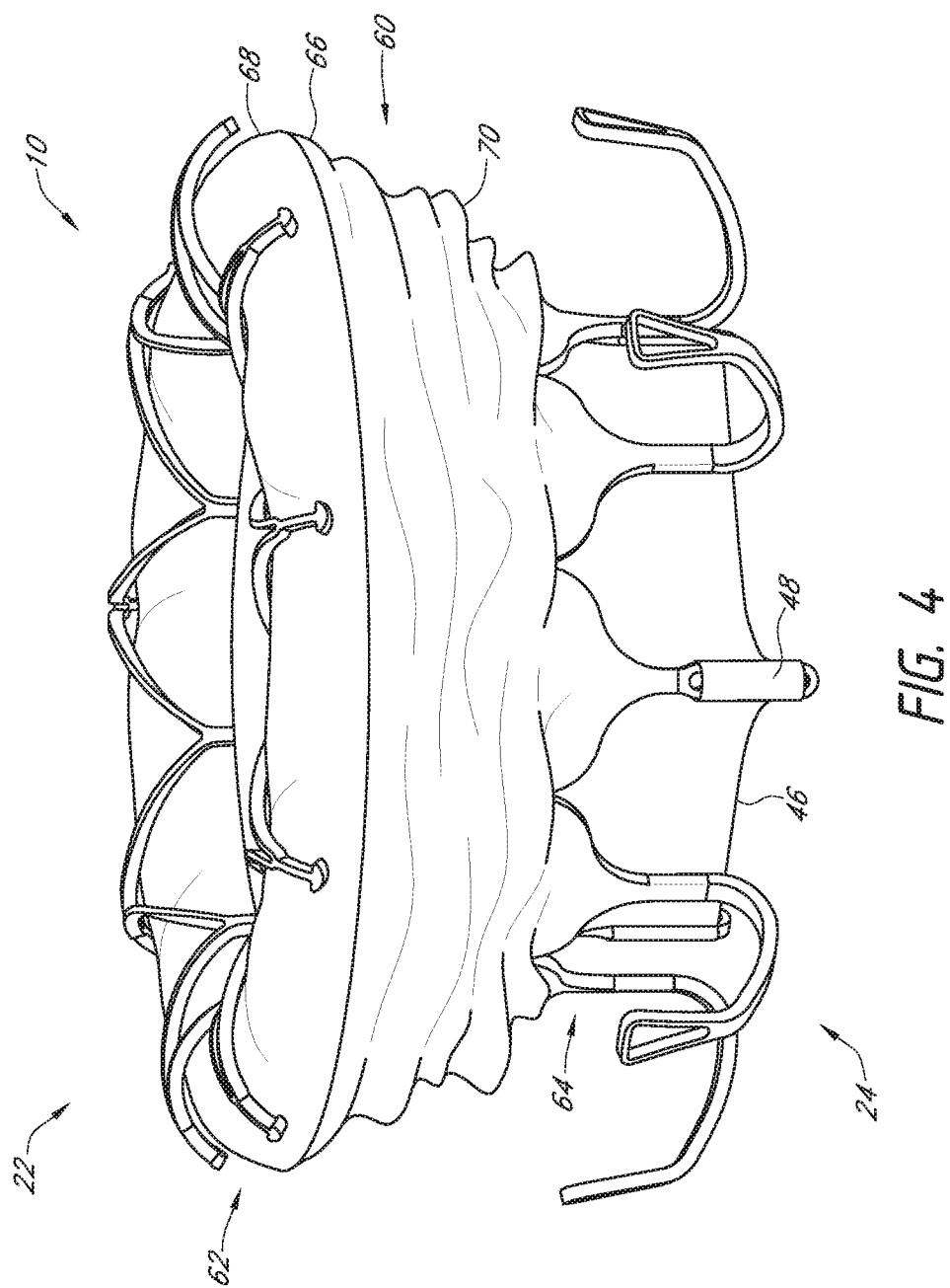
FIG. 4 is a perspective view of the prosthesis of FIG. 3, with an embodiment of a flap assembly attached thereto.
Figure 5:
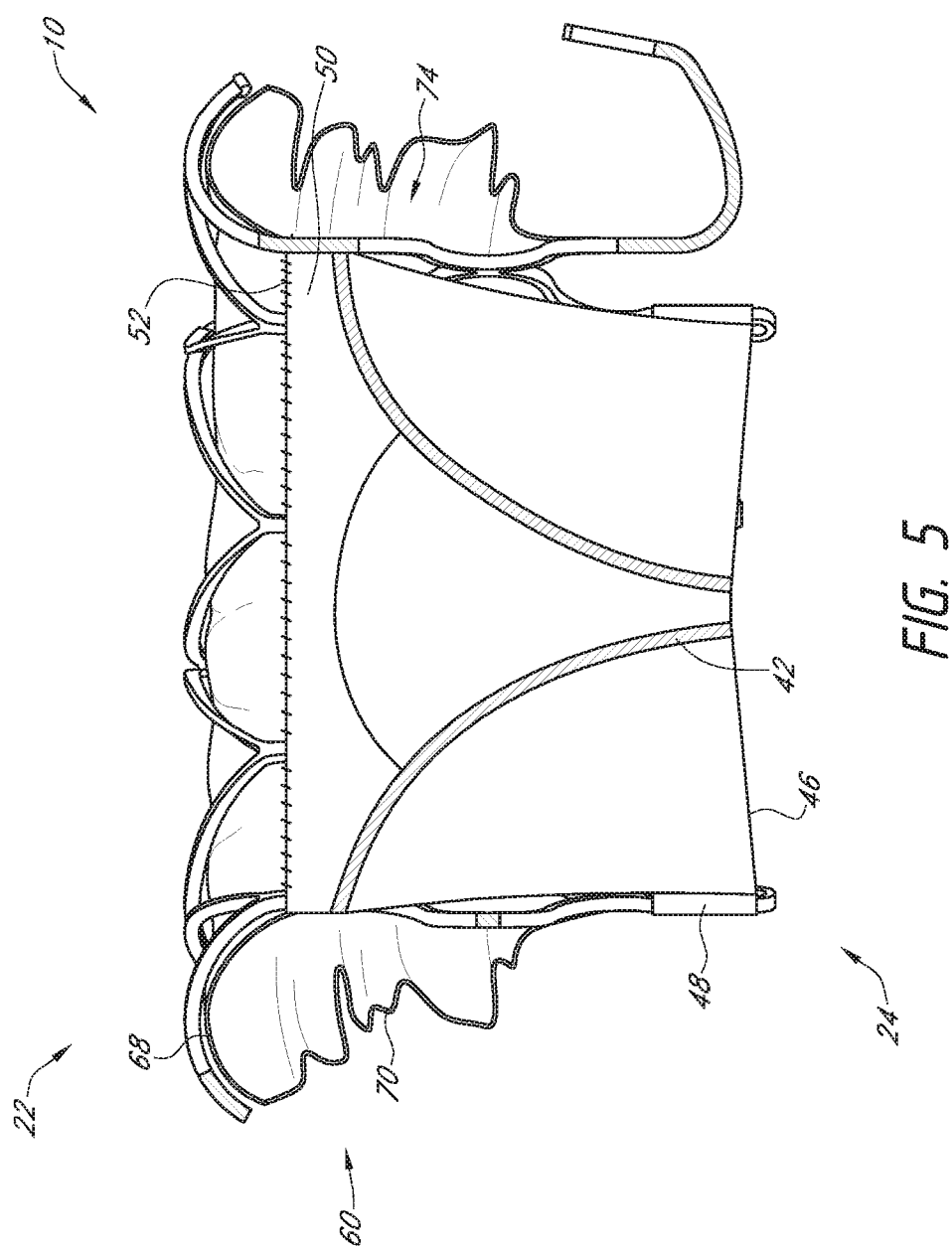
FIG. 5 is a partial, cross-sectional view of the prosthesis of FIG. 4.

With reference next to the embodiment of FIGS. 4 and 5, the prosthesis 10 can include a flap or sail assembly 60 which can be positioned around and secured to an exterior of the frame 20. The flap assembly 60 can be annular and can extend entirely circumferentially around the frame 20. The flap assembly 60 can prevent or inhibit backflow of fluids around the prosthesis 10. For example, with the flap assembly 60 positioned annularly around an exterior of the frame 20, the flap assembly 60 can create an axial barrier to fluid flow exterior to the frame 20 when deployed within a body cavity. As shown, the flap assembly 60 can form a flange 66 when the flap assembly 60 is positioned within a body cavity, such as a native valve, with the flange 66 sealing against at least a portion of tissue surrounding the body cavity. In addition, the flap assembly 60 can encourage tissue in-growth between the flap assembly 60 and the natural tissue. This may further help to prevent leakage of blood flow around the prosthesis 10.

The flap assembly 60 can have a first end 62 positioned at or proximate a first end 22 of the frame 20 and extend to a second end 64 positioned at or proximate a second end 24 of the frame 20. In some embodiments, the second end 64 of the flap assembly 60 can be provided with a generally straight edge with extends circumferentially around the frame 20. It is also contemplated that other configurations, such as a curved edge, can also be used as desired. In some embodiments, the second end 64 can follow the shape of the struts along the second end 24 of the frame 20.

As shown in the illustrated embodiment, the flap assembly 60 can form a flange 66. The flange 66 can extend generally radially outward in a direction generally orthogonal to the longitudinal axis of the frame 20. In some embodiments, the flange 66 can also project towards the first end 22 and/or second end 24 of the frame 20. The flange 66 can be used to further prevent or inhibit backflow of fluids around the prosthesis 10. As noted above, the flange 66 can be formed when the flap assembly 60 is positioned within the body cavity, such as a native valve 80.

The flap assembly 60 can include a first portion 68 which extends radially outward from the frame 20 and a second portion 70 which extends from the first portion 68 in a direction generally towards an opposing end of the frame 20. The first portion 68 can extend along an exterior portion of the frame 20 as shown. For example, the first portion 68 can extend along the flared or shoulder portion 28 of the frame 20. The first portion 68 can follow a curvature of the frame 20 and can form a funnel which assists in directing fluid flow through an interior of the frame 20 where fluid can pass through the valve 40. The first portion 68 can be attached to the end 52 of the liner 50 at a first end of the first portion 68 using any mechanism or technique as described above, such as via sutures and/or adhesives. As shown in the illustrated embodiment, the first portion 68 can extend up to or proximate the elongate tips 33 although it is contemplated that the first portion 68 can extend only partially towards the elongate tips 33 or can extend beyond the elongate tips 33.

The second portion 70 can extend from the first portion 68 towards an opposing end of the frame 20. For example, as shown in the illustrated embodiment, the second portion 70 can extend from the first portion 68 at or proximate the first end 22 of the frame 20 and extend towards the second end 24 of the frame 20. In the illustrated embodiment, the second portion 70 extends up to or proximate the second end 24 of the frame 24 although it is also contemplated that the second portion 70 can extend only partially towards the second end 24 or can extend beyond the second end 24. For example, the second portion 70 can extend up to an intermediate portion of the frame 20 between the first end 22 and the second end 24 of the frame 20. As another example, the second portion 70 can extend beyond or over the second end 24 of the frame 20. In some embodiments, the second portion 70 can extend along and/or over a portion of the second anchoring feature 34. As shown in the illustrated embodiment, fluid can flow around the flap 60 and into the space 74 formed between the liner 50, first portion 68, and the second portion 70.

In some embodiments, the first portion 68 and/or the second portion 70 can be formed from a material such as such as knit polyester (e.g., polyethylene terephthalate (PET)) or any other biocompatible material such as those which are wholly or substantially fluid impermeable, flexible, stretchable, deformable, and/or resilient. The first portion 68, second portion 70, and/or the liner 50 may be made from the same or similar materials. As shown in the illustrated embodiment, the first portion 68 and the second portion 70 can be formed as separate components and can be attached together using any mechanism or technique as described above, such as via sutures and/or adhesives. In other embodiments, the first portion 68 and second portion 70 can be a single component. The flap assembly 60 may be attached to the frame 20 using similar mechanisms and/or techniques. For example, the first end 62 and the second end 64 of the flap assembly 60 can be attached to struts and/or anchoring features 32, 34 of the frame 20 via sutures. The flap assembly 60 can also include other structures, such as wires formed from resilient materials such as nitinol, to allow at least portions of the flap assembly 60 to retain a particular shape. These structures may be positioned on an inner surface of the flap assembly 60.

Figure 6:
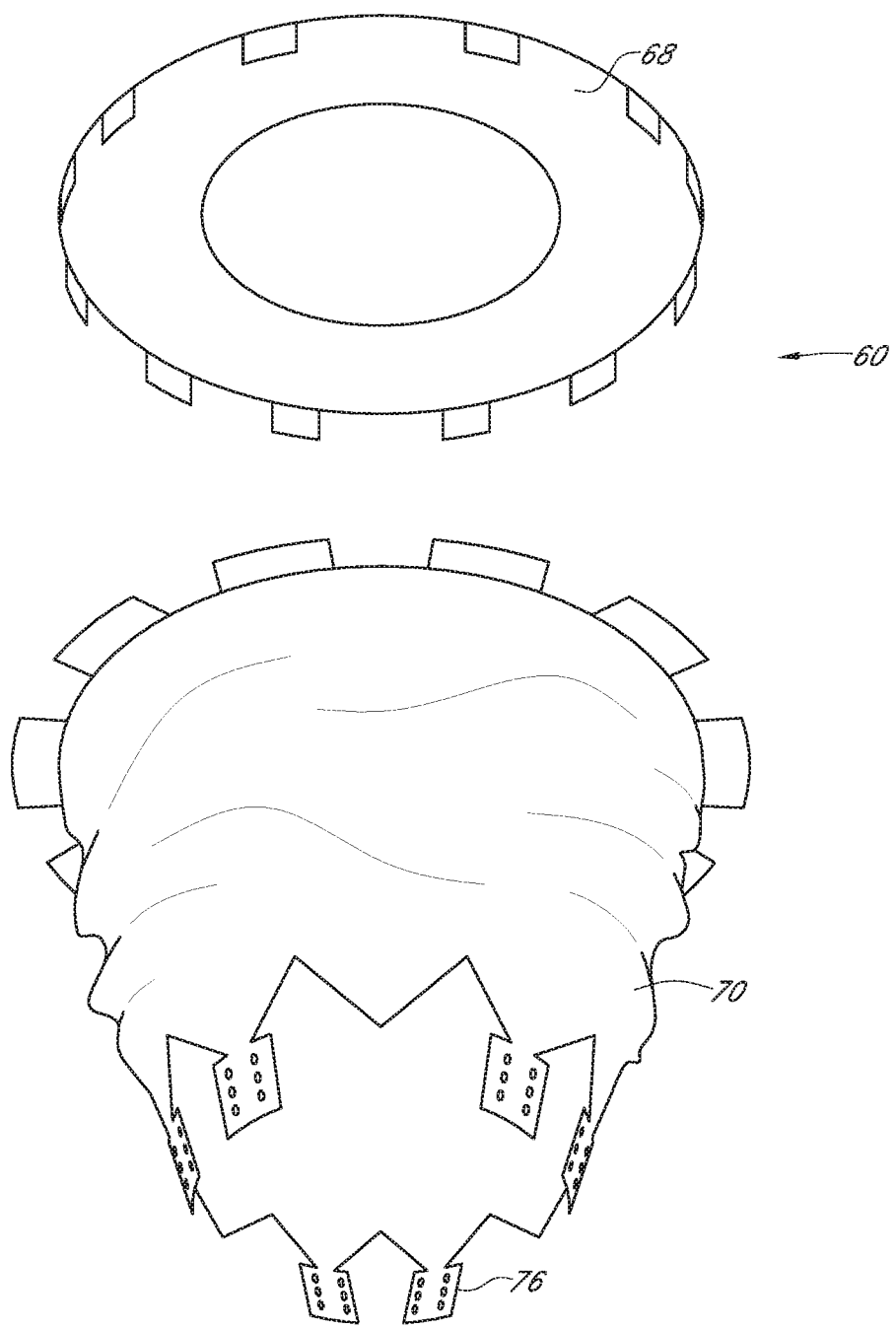
FIG. 6 is a perspective view of an embodiment of a flap assembly.

As noted above, the flap assembly 60 can be attached to the frame 20, the first anchoring feature 32, and/or the second anchoring feature 34 in many different ways. For example, the flap assembly 60 can be sewn to the frame 20, the valve 40, and/or the liner 50. In the embodiment illustrated in FIGS. 4 and 5, the first portion 68 is attached to the first anchoring feature 32 and the second portion 70 is attached to the struts of frame 20 using sutures. In other embodiments (not shown), the flap assembly 60 is only attached to the frame 20 along the second end 64 of the flap assembly 60, and the first portion 68 remains unattached to any portion of the frame 20 or any anchoring features 32, 34. In other embodiments, a plurality of circumferentially spaced tabs 76 (as shown in the embodiment of FIG. 6) can be used to attach the flap assembly 60 to portions of the anchors of the second anchoring feature 34. The tabs can be wrapped around the anchors. The tabs 76 themselves may also form sleeves that are configured to surround at least a portion of the anchors. In some embodiments, the anchors, such as anchor of anchoring features 32, 34, can include eyelets that may be used to secure the flap assembly 60 to the anchor. The tab 76 can be attached to the eyelet using any mechanism or technique described above, for example by stitching.

Figure 11:
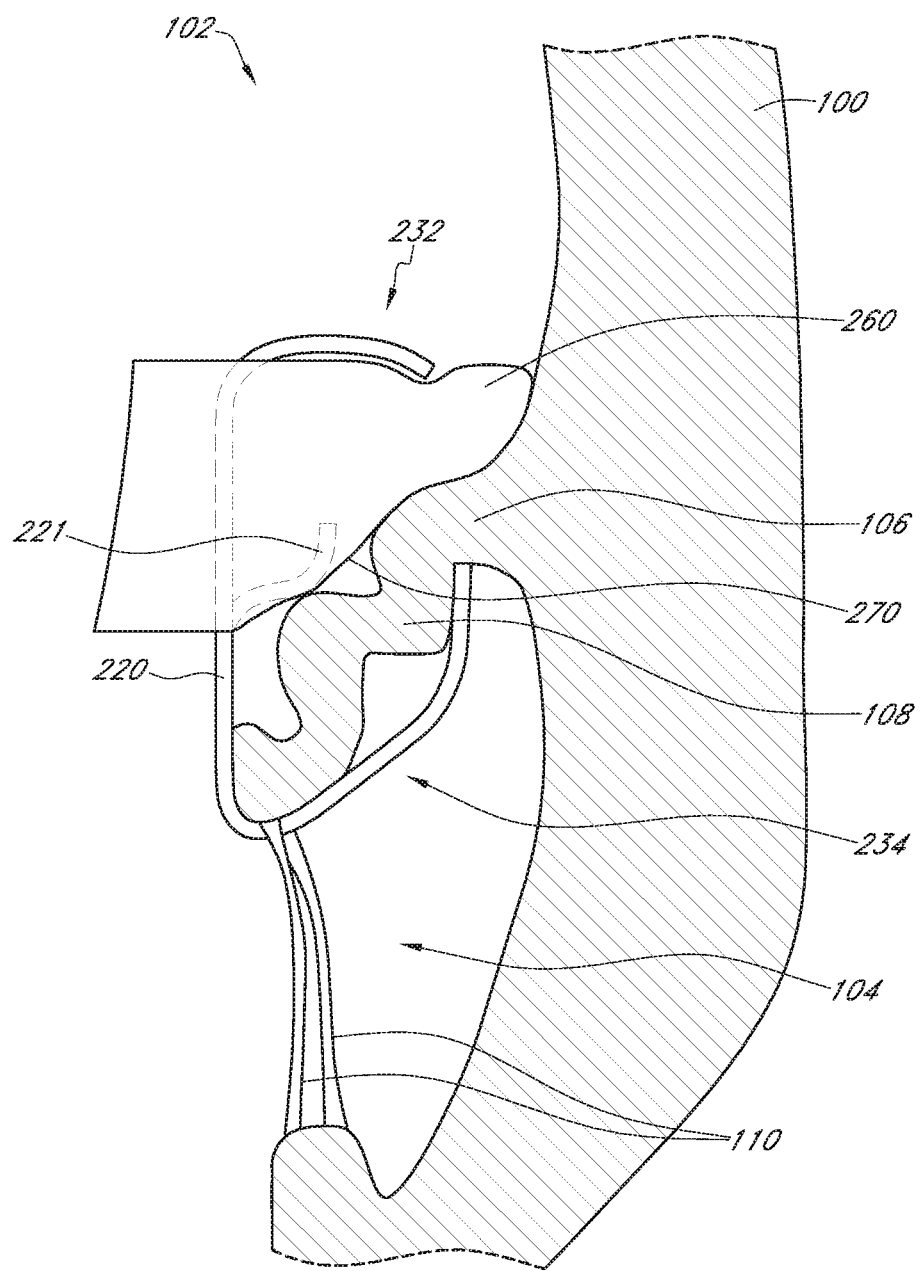
FIG. 11 illustrates a schematic representation of the prosthesis of FIG. 10 positioned within a heart.
Figure 12:
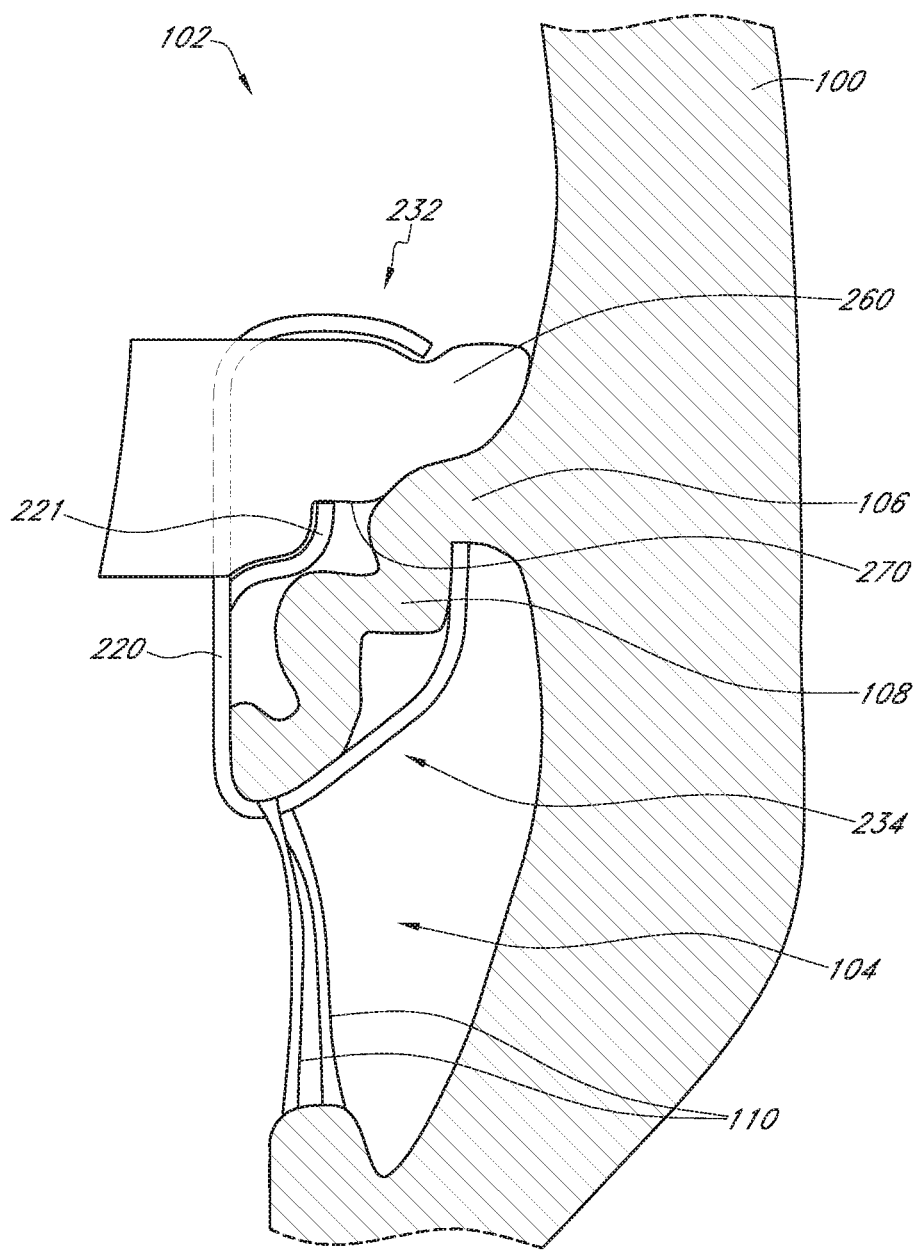
FIG. 12 illustrates a schematic representation of another embodiment of a prosthesis positioned within a heart.
Figure 14:
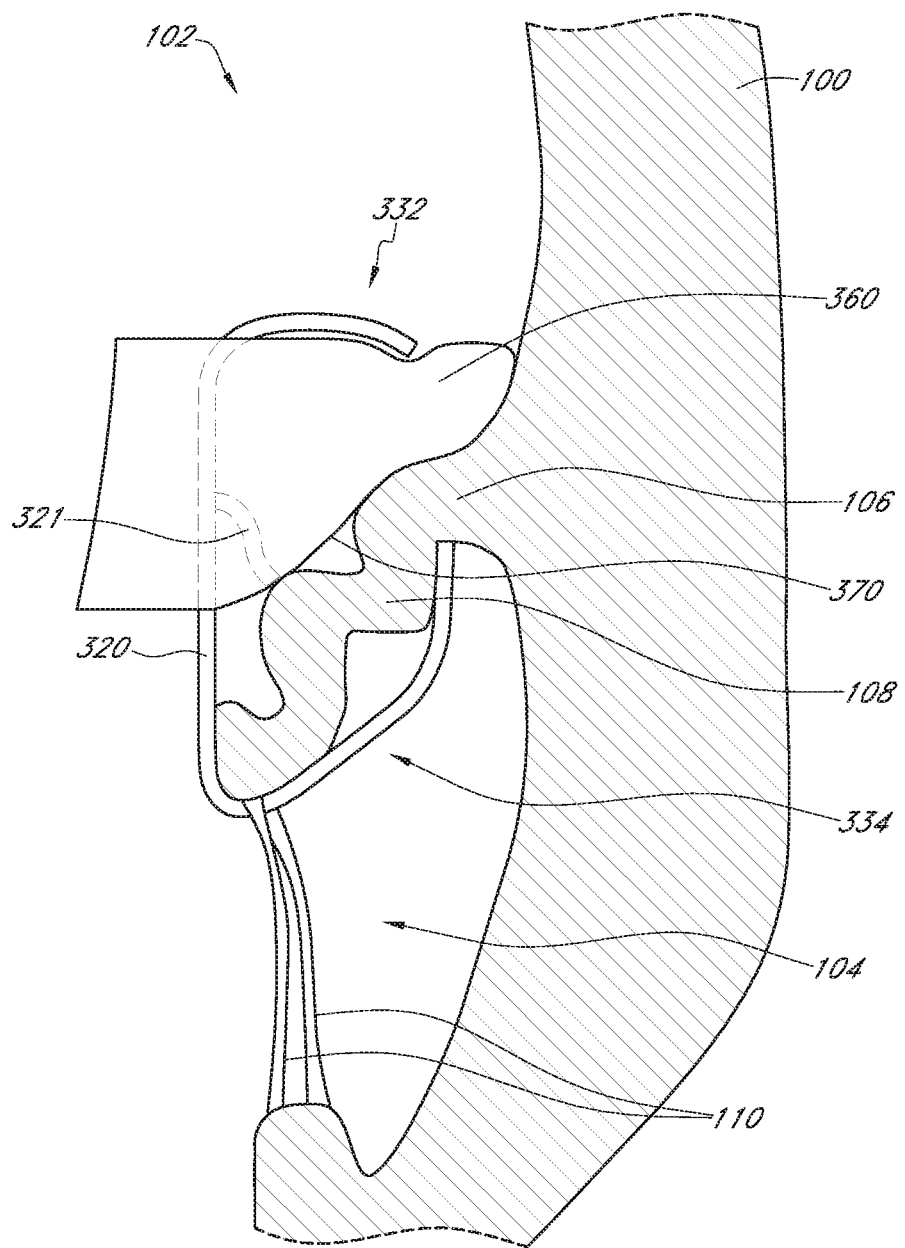
FIG. 14 illustrates a schematic representation of the prosthesis of FIG. 13 positioned within a heart.

Reference is now made to FIGS. 7A-9 which illustrate schematic representations of an embodiment of the prosthesis 10 positioned within a native mitral valve of a heart 100. A portion of the native mitral valve is shown schematically and represents typical anatomy, including a left atrium 102 positioned above an annulus 106 and a left ventricle 104 positioned below the annulus 106. The left atrium 102 and left ventricle 104 communicate with one another through a mitral annulus 106. Also shown schematically in FIGS. 7A-9 is a native mitral leaflet 108 having chordae tendineae 110 that connect a downstream end of the mitral leaflet 108 to the papillary muscle of the left ventricle 104. The portion of the prosthesis 10 disposed upstream of the annulus 106 (toward the left atrium) can be referred to as being positioned supra-annularly. The portion generally within the annulus 106 is referred to as positioned intra-annularly. The portion downstream of the annulus 106 is referred to as being positioned sub-annularly (toward the left ventricle). While the mitral leaflet 108 is illustrated in a relatively unwrinkled state, it should be understood that the mitral leaflet 108 may be in a relatively wrinkled state such as is shown in FIGS. 11, 12 and 14.

Figure 7A:
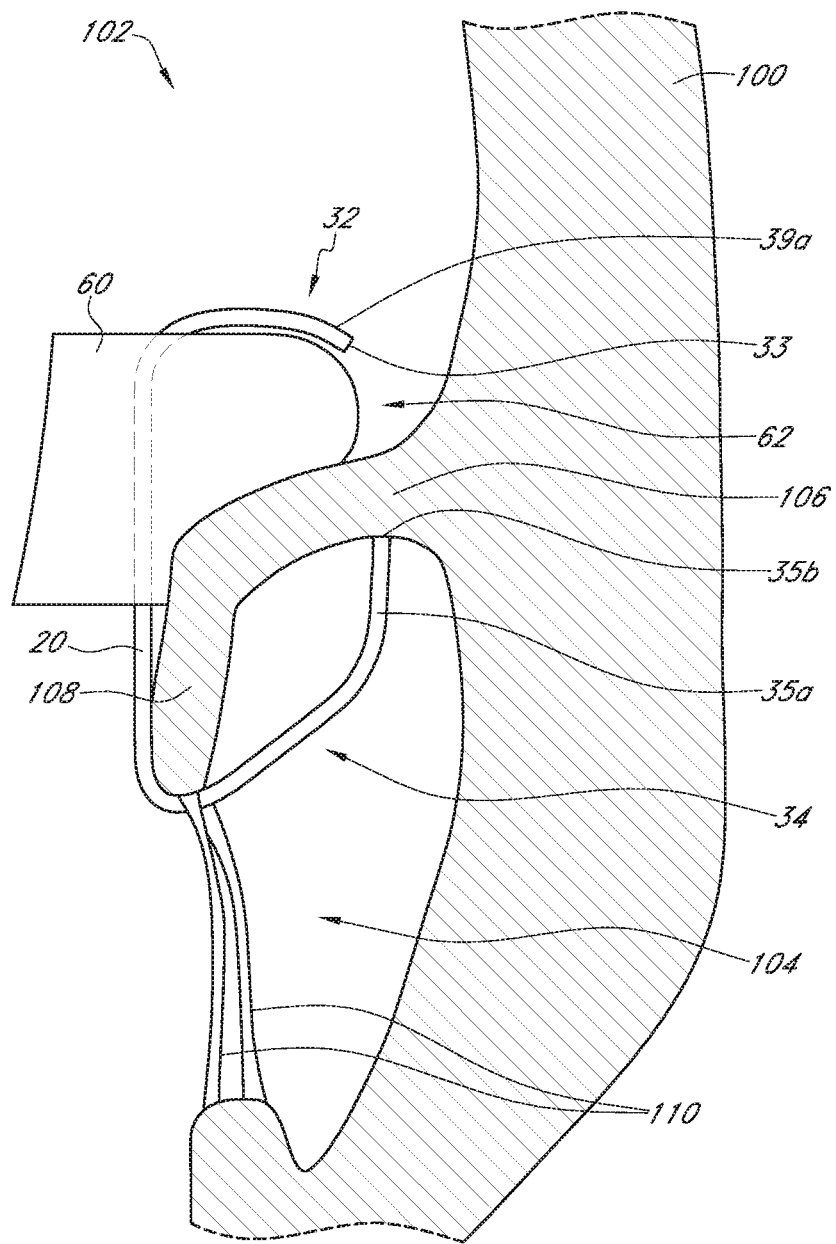
FIGS. 7A-9 illustrate schematic representations of the prosthesis of FIG. 4 positioned within a heart, with FIGS. 7A-7C illustrating the prosthesis in situ with distal anchors contacting the ventricular side of a mitral valve annulus, FIG. 8 illustrating the prosthesis in situ with distal anchors not contacting the ventricular side of the mitral valve annulus, and FIG. 9 illustrating the prosthesis in situ with distal anchors not extending between the chordae tendineae.
Figure 7B:
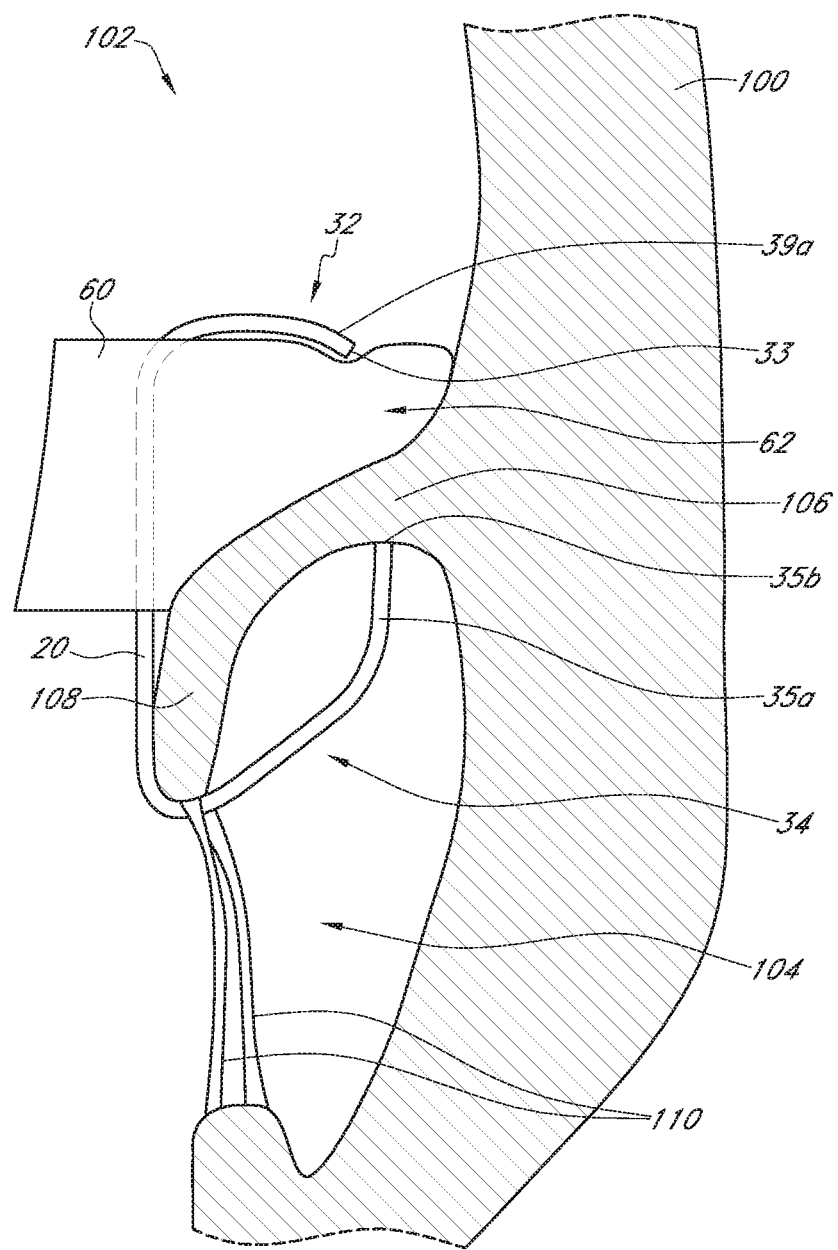
Figure 7C:
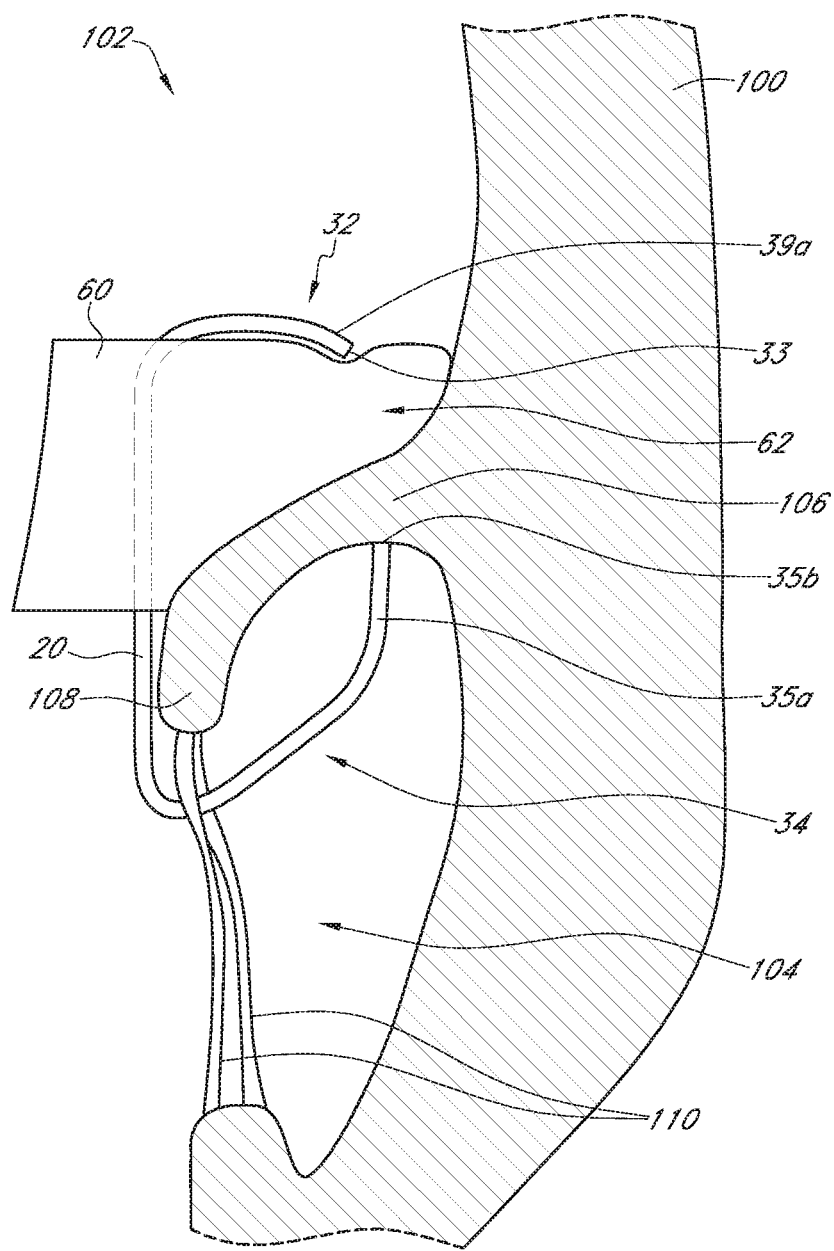
Figure 8:
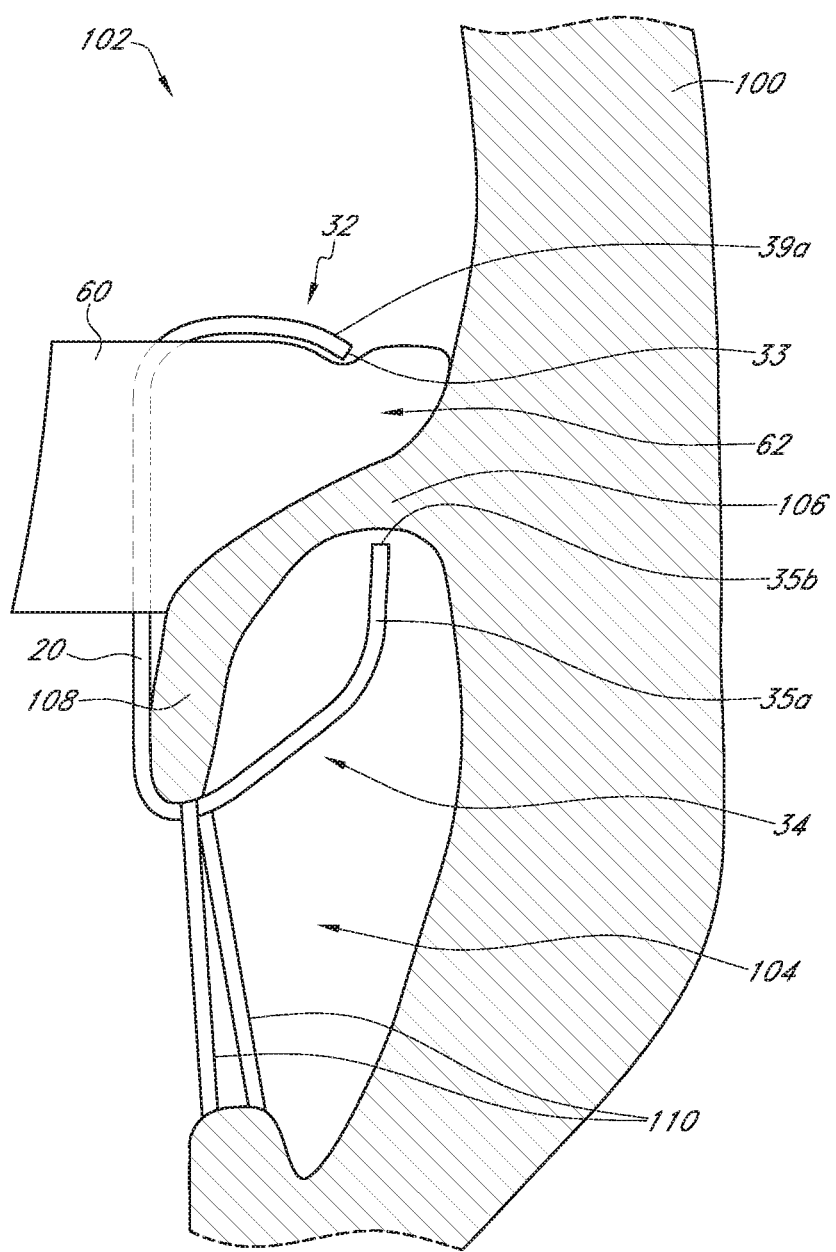
Figure 9:
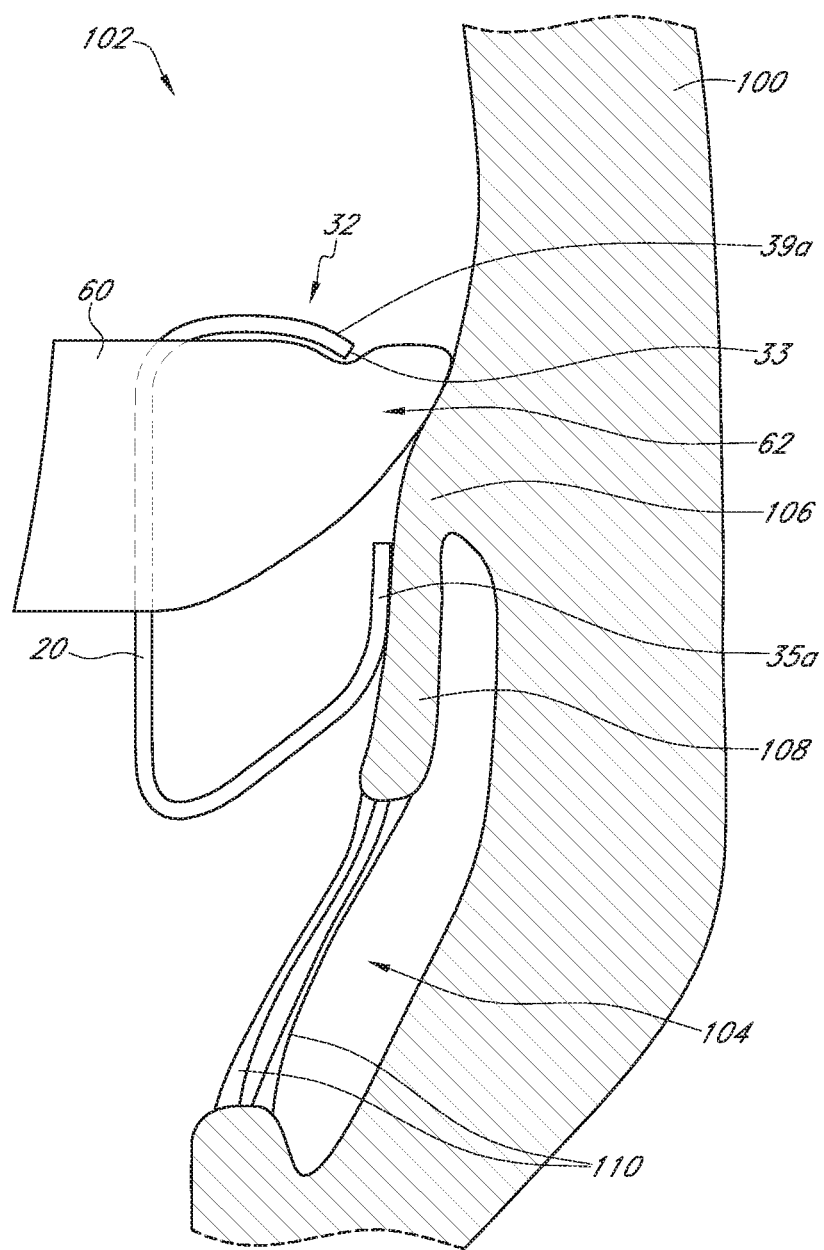

As shown in the situations illustrated in FIGS. 7A-8, the replacement heart valve 10 can be disposed so that the mitral annulus 106 is between the first anchoring feature 32 and the second anchoring feature 34. In some situations, the prosthesis 10 can be positioned such that ends or tips 35*b* of the anchors 35*a* contact the annulus 106 as shown, for example, in FIGS. 7A-7C. In some situations, the prosthesis 10 can be positioned such that ends or tips 35*b* of the anchors 35*a* do not contact the annulus 106 as shown, for example, in FIG. 8A. In some situations, the prosthesis 10 can be positioned such that the portions of the second anchoring feature 34a, such as one or more anchors 35b, do not extend around the leaflet 108 as shown in FIG. 9. While FIGS. 7A-9 are described separately below, it should be understood that one or more of the situations illustrated in 7A-9 may be present when the prosthesis 10 is positioned at the implantation location, such as a native mitral valve. For example, in some situations the prosthesis 10 may be positioned such that some portions of the first anchoring feature 32 may contact the annulus 106 while other portions of the first anchoring feature 32 may not and/or such that some portions of the second anchoring feature 34 may contact the annulus 106 while other portions of the second anchoring feature 34 may not.

With reference first to the situations illustrated in FIGS. 7A-8, the prosthesis 10 can be positioned so that the ends or tips 35b of the anchors 35a of the second anchoring feature 34 are on a ventricular side of the mitral annulus 106 and the ends or tips 33, 39a of the first anchoring feature 32 are on an atrial side of the mitral annulus 106. The distal anchors 30 can be positioned such that the ends or tips 32 of the distal anchors 30 are on a ventricular side of the native leaflets beyond a location where chordae tendineae 110 connect to free ends of the native leaflets. The anchors 35a may extend between at least some of the chordae tendineae 110 and, in some situations such as those shown in FIGS. 7A-7C, can contact or engage a ventricular side of the annulus 106. It is also contemplated that in some situations, such as those shown in FIG. 8, the anchor 35a may not contact the annulus 106, though the anchors 35b may still contact the native leaflet 108. In some situations, the anchors 35a can contact tissue of the left ventricle 104 beyond the annulus 106 and/or a ventricular side of the leaflets.

During delivery, the anchors 35a (along with the frame 20) can be moved toward the ventricular side of the annulus 106 with the anchors 35a extending between at least some of the chordae tendineae 110 to provide tension on the chordae tendineae 110. The degree of tension provided on the chordae tendineae 110 can differ. For example, little to no tension may be present in the chordae tendineae 110 as shown in FIG. 7C where the leaflet 108 is shorter than or similar in size to the anchors 35a. A greater degree of tension may be present in the chordae tendineae 110 as shown in FIGS. 7A and 7B where the leaflet 108 is longer than the anchors 35a and, as such, takes on a compacted form and is pulled proximally. An even greater degree of tension may be present in the chordae tendineae 110 as shown in FIG. 8 where the leaflets 108 are even longer relative to the anchors 35a. As shown in FIG. 8, the leaflet 108 is sufficiently long such that the anchors 35a do not contact the annulus 106.

The first anchoring feature 32 can be positioned such that the ends or tips 33, 39a of the first anchoring feature 32 are adjacent the atrial side of the annulus 106 and/or tissue of the left atrium 102 beyond the annulus 106. In some situations, some or all anchors of the first anchoring feature 32 may only occasionally contact or engage the atrial side of the annulus 106 and/or tissue of the left atrium 102 beyond the annulus 106. For example, as shown in FIGS. 7A and 7B, the first anchoring feature 32 may be spaced from the atrial side of the annulus 106 and/or tissue of the left atrium 102 beyond the annulus 106. The first anchoring feature 32 could provide axial stability for the prosthesis 10. In some situations such as those illustrates, some or all of the anchors of the first anchoring feature 32 may contact the flap assembly 60. In some situations, it is contemplated that some or all of first anchoring feature 32 may not contact the flap assembly 60. This may occur when the flap assembly 60 is in a collapsed configuration although it may also occur when the flap assembly 60 is in an expanded configuration. It is also contemplated that some or all of the first anchoring feature 32 may contact the atrial side of the annulus 106 and/or tissue of the left atrium 102 beyond the annulus 106

With continued reference to the situations illustrated in FIGS. 7A-8, the flap assembly 60 can be positioned such that the first end 62 of the flap assembly 60 is positioned along or adjacent an atrial side of the annulus 106. The first end 62 can be positioned between the atrial side of the annulus 106 and the first anchoring feature 32. The first end 62 can extend radially outward such that the flap assembly 60 is positioned along or adjacent tissue of the left atrium 102 beyond the annulus 106. The flap assembly 60 can create a seal over the atrial side of the annulus 106 when the flap assembly 60 is in an expanded state. The flap assembly 60 may also create a seal over the atrial side of the annulus 106 when the flap assembly is in a collapsed state.

The flap assembly 60 can transition from the collapsed state to the expanded state during systole when pressure in the left ventricle 104 increases. This increased pressure within the left ventricle 104 can cause blood within the left ventricle 104 to be directed to areas of lower pressure, such as the aorta (not shown) and the left atrium 102. As noted above, during systole the valve 40 may be closed to prevent blood from flowing back into the left atrium 102. A substantial portion of blood can forced around the frame 20 and valve 40 and into the flap assembly 60 such that the flap assembly 60 can expand. Sealing along an atrial side of the annulus 106 can be particularly effective. The left atrium 102 can be at a lower pressure in comparison to the pressure of the space 74 between the flap assembly 60 and the valve 40, which is closer to the pressure of the left ventricle 104. The existence of such a pressure differential between the left atrium 102 and the space 74 during systole can allow the flap assembly 60 to apply a greater force to surrounding tissue within the left atrium 102. During diastole, where blood flows from the left atrium 102 towards the left ventricle 104, the flap assembly 60 can transition from the expanded state back to the collapsed state.

In some situations such as those shown in FIGS. 7A and 8, the flap assembly 60 may not contact the wall of the heart 100. This may occur when the flap assembly 60 is in a collapsed configuration although it may also occur when the flap assembly 60 is in an expanded configuration. In some situations such as those shown in FIGS. 7B and 7C, the flap assembly 60 may contact the wall of the heart 100. This may occur when the flap assembly 60 is in an expanded configuration although it may also occur when the flap 60 is in a collapsed configuration. As shown in FIGS. 7A-8, the flap assembly 60 can also assist in filling gaps which exist between the leaflet 108 and the frame 20 (portions of which are illustrated in dashed lines).

In some situations such as that shown in FIG. 9, the leaflet 108 may not be captured between the frame 20 (portions of which are shown in dashed lines) and the one or more anchors of the second anchoring feature 34. As shown, the anchor 35a may be positioned along an atrial surface of the leaflet 108. The anchor 35a may also be positioned along an inner surface of the annulus 106. It is also contemplated that the anchor 35a may exert a force against the leaflet 108 such that the leaflet 108 is pushed radially outward, relative to the longitudinal axis of the frame 20, towards a wall of the heart 100. In such situations, the flap assembly 60 can create a seal intra-annularly and/or along an atrial side of the leaflet 108.

In alternative situations (not shown), the flap assembly 60 can create a seal along a ventricular side of the annulus 106. For example, the prosthesis 10 may be disposed in the mitral annulus such that a portion of the flap assembly 60 is positioned on the ventricular side of the native annulus 106.

As noted above, although the in vivo situations of FIG. 7A-9 have been described separately, it should be understood that one or more of these situations may be present when a prosthesis is positioned at the implantation location, such as a native mitral valve. For example, one or more of the anchors of the second anchoring feature 34 may not capture the leaflet 108 whereas the remaining anchors 30 of the second anchoring feature 34 may capture the leaflet 108. As another example, when the prosthesis 10 is positioned within the native mitral valve, the flap assembly 60 can contact the wall of the heart 100 along one or more portions of an outermost circumference of the first end 62 and may not contact the wall of the heart 100 along other portions of the outermost circumference of the first end 62. For example, the flap assembly 60 may contact the wall of the heart 100 along an approximately 180 degree portion of the outermost circumference of the first end 62 and may not contact the wall of the heart 100 along the remaining, approximately 180 degree portion of the outermost circumference of the first end 62.

Figure 10:
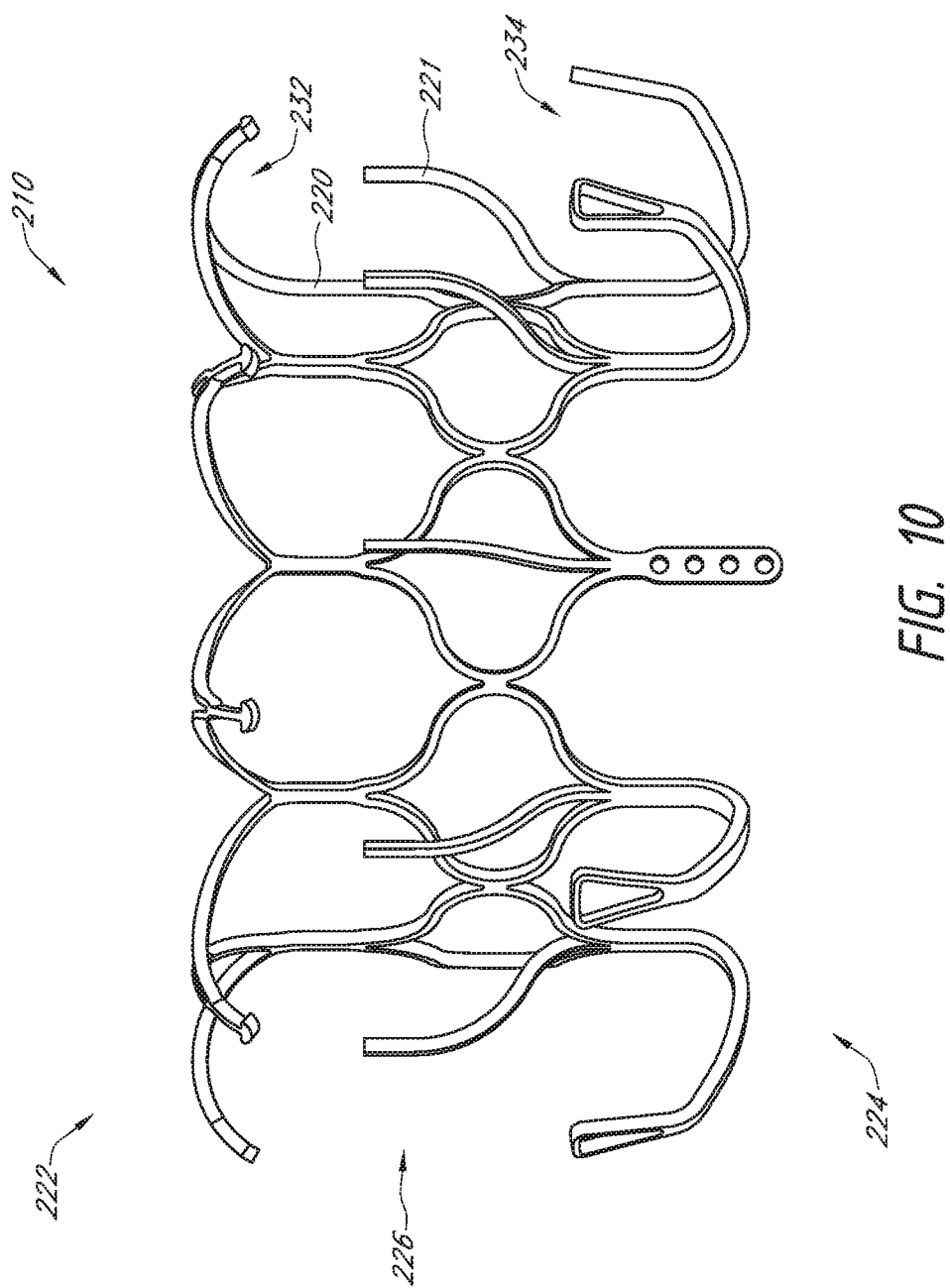
FIG. 10 is a side view of another embodiment of a prosthesis, illustrating a half of the prosthesis.

With reference next to the embodiment of FIGS. 10 and 11, the prosthesis 210 can have a similar construction to prosthesis 10. Prosthesis 210 can include arms 221 positioned along the frame 220 between the first end 222 and the second end 224. The arms 221 can extend radially outward from the longitudinal axis of the frame 220 when the frame 220 is in an expanded configuration. As shown in the illustrated embodiment, the arms 221 can extend from the frame 220 in a direction towards the first end 222 of the frame 220. The arms 221 can contact a flap assembly, such as flap assembly 260, to bias the flap assembly towards an inflated or expanded configuration even in the absence of fluid within the flap assembly. For example, the arms 221 can support the flap assembly 260 and reduce the likelihood of deflation or collapse during the diastolic cycle.

Reference is now made to FIG. 11 which illustrates a schematic representation of an embodiment of the prosthesis 210 having an flap assembly 260 positioned within a native mitral valve of a heart 100. As shown in the illustrated embodiment, arms 221 can contact the flap assembly 260 along the second portion 270 of the flap assembly 260. Accordingly, the flap assembly 260 can be biased towards the inflated configuration via both the arms 221 and the first anchoring feature 232 to which the flap assembly 260 can be attached. The radial distance of arms 221 from the longitudinal axis of the frame 220 can be chosen such that the flap assembly 260 is placed at or proximate tissue of the body cavity. For example, the radius of the arms 221 can be chosen such that the flap assembly 260 contacts or is proximate the leaflets 108 of the mitral valve. While the mitral leaflet 108 is illustrated in a relatively wrinkled state, it should be understood that the mitral leaflet 108 may be in a relatively unwrinkled state such as is shown in FIGS. 7A-9.

In some embodiments, the radial distance of arms 221 from the longitudinal axis passing through the middle of the frame 220 may be about 110% or more, about 120% or more, about 130% or more, about 140% or more, or about 150% or more of the radius of the middle portion 226 of the frame 220 when the frame 220 and the anchoring features 232, 234 are in expanded configurations. For example, if the radius of the middle portion 226 of the frame 220 is 15 mm and an arm 221 is spaced 5 mm from the exterior of the middle portion 226 of the frame 220, the arm 221 extends 20 mm from the longitudinal axis of the frame 220, and is 133.33% of the radius of the frame 220. To reduce the overall radial dimension of the frame 220 during delivery to the body cavity, the arms 221 can be bent inwardly towards the frame 220 when the frame 220 is in a collapsed configuration.

Although the embodiment of FIGS. 10 and 11 include an arm 221 positioned within the interior of the flap assembly 260, it is also contemplated that the arm 221 can be positioned outside of or exterior to the flap assembly 260. For example, the arm 221 can be positioned along an exterior surface of the flap assembly 260 as shown in FIG. 12. The flap assembly 260 may be attached to the arm 221 using any suitable mechanism or technique described above, such as via sutures. While the mitral leaflet 108 is illustrated in a relatively wrinkled state in FIG. 12, it should be understood that the mitral leaflet 108 may be in a relatively unwrinkled state such as is shown in FIGS. 7A-9.

Figure 13:
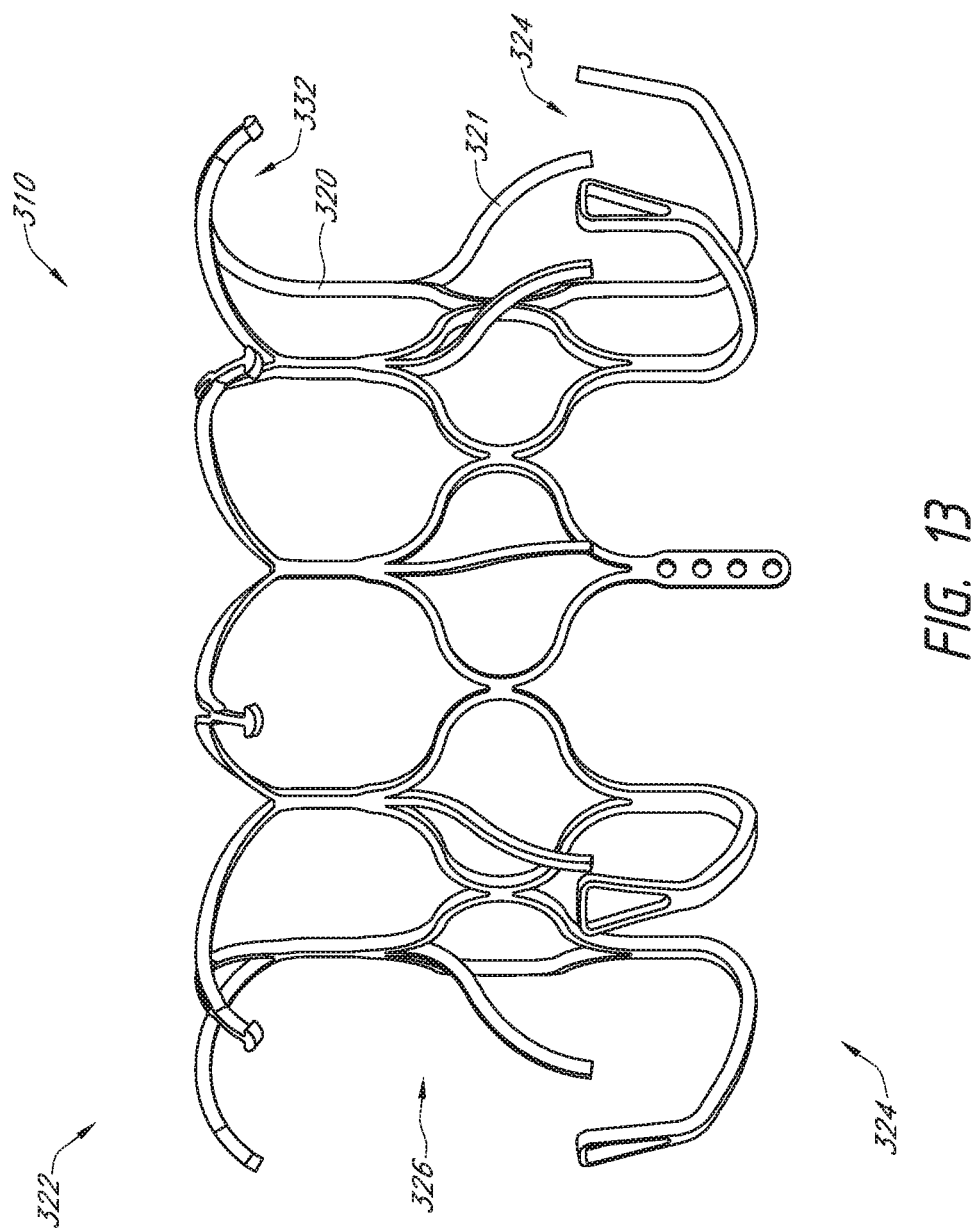
FIG. 13 is a side view of another embodiment of a prosthesis, illustrating a half of the prosthesis.

With reference next to the embodiment of FIGS. 13 and 14, the prosthesis 310 can have a similar construction to prostheses 10, 210. Prosthesis 310 can include arms 321 positioned along the frame 320 between the first end 322 and the second end 324. The arms 321 can extend radially outward from the longitudinal axis of the frame 320 when the frame 320 is in an expanded configuration. As shown in the illustrated embodiment, the arms 321 can extend from the frame 320 in a direction towards the second end 324 of the frame 320. The arms 321 can contact a flap assembly, such as flap assembly 360, to bias the flap assembly towards an inflated or expanded configuration even in the absence of fluid within the flap assembly. For example, the arms 321 can support the flap assembly 360 and reduce the likelihood of deflation or collapse during the diastolic cycle.

Reference is now made to FIG. 14 which illustrates a schematic representation of an embodiment of the prosthesis 310 having an flap assembly 360 positioned within a native mitral valve of a heart 100. As shown in the illustrated embodiment, arms 321 can contact the flap assembly 360 along the second portion 370 of the flap assembly 360. Accordingly, the flap assembly 360 can be biased towards the inflated configuration via both the arms 321 and the first anchoring feature 332 to which the flap assembly 360 can be attached. The radial distance of arms 321 from the longitudinal axis of the frame 320 can be chosen such that the flap assembly 360 is placed at or proximate tissue of the body cavity. For example, the radius of the arms 321 can be chosen such that the flap assembly 360 contacts or is proximate the leaflets 108 of the mitral valve. While the mitral leaflet 108 is illustrated in a relatively wrinkled state, it should be understood that the mitral leaflet 108 may be in a relatively unwrinkled state such as is shown in FIGS. 7A-9.

Figure 15:
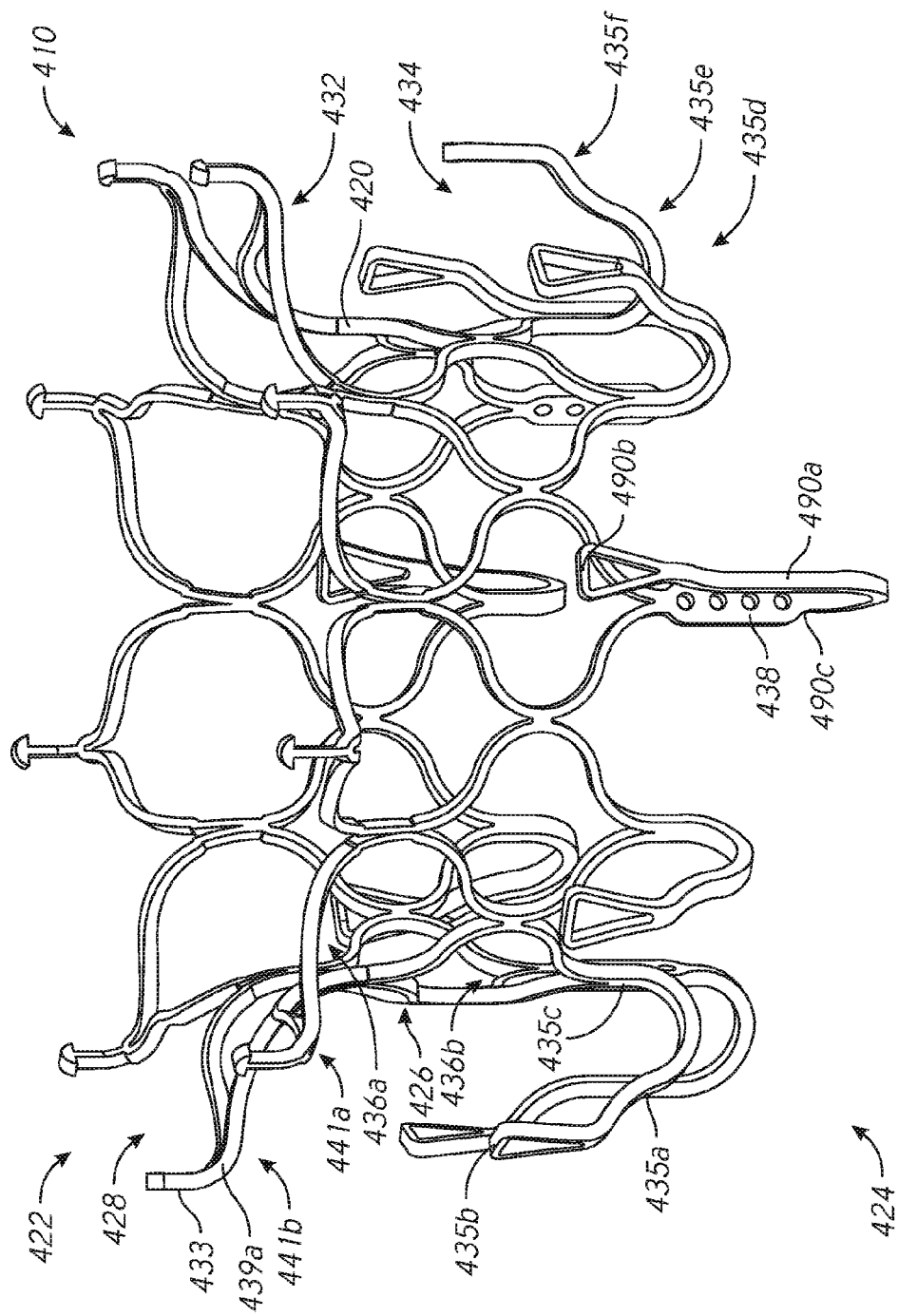
FIG. 15 is a perspective view of another embodiment of a prosthesis.
Figure 16:
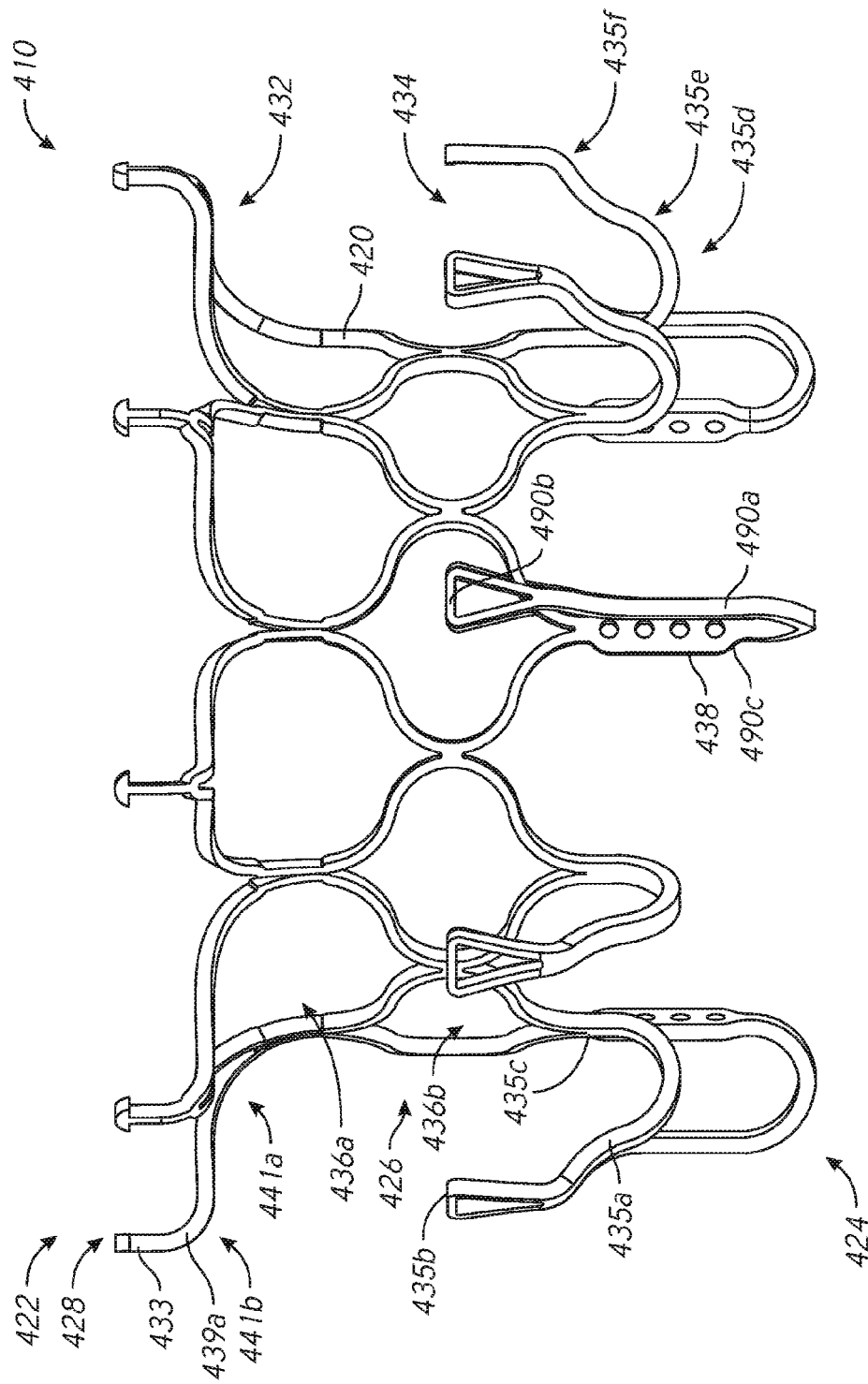
FIG. 16 is a side view of the prosthesis of FIG. 15.

With reference next to the embodiment of FIGS. 15 and 16, the prosthesis 410 can have a similar construction to prostheses 10, 210, 310. Prosthesis 410 can include a frame 420, the frame 420 having a first end 422, a second end 424, a middle or intermediate portion 426, a first anchoring feature 432 and a second anchoring feature 434. Similar to prostheses 10, 210, 310, one or both anchoring features 432, 434 can contact or engage a native valve annulus, such as the native mitral valve annulus, tissue beyond the native valve annulus, native leaflets, and/or other tissue at or around the implantation location. In some embodiments, the first anchoring feature 432 can be positioned on an atrial side of the native mitral valve annulus and the second anchoring feature 434 can be positioned on a ventricular side of the native mitral valve annulus. While the anchoring features 432, 434 have been illustrated as extending from the first and second ends 422, 424 of the frame 420 respectively, it should be understood that the anchoring features 432, 434 can be positioned along any other portion of the frame 420 as desired. Moreover, while two anchoring features 432, 434 have been included in the illustrated embodiment, it is contemplated that fewer or greater sets of anchoring features can be utilized.

One or more struts 438 of the frame 420 can include eyelets. As illustrated, a plurality of eyelets are located along the strut 438 and extend along a single row. Similar to struts 38, the eyelets may be used to attach features such as a valve 40, a liner 50, and/or a flap or sail assembly 60 to the frame 420. As also shown in the illustrated embodiment, the struts 438 having eyelets can extend from a distal-most end of cells in a direction parallel with the longitudinal axis of the frame 420, although it is also contemplated that the struts 438 similar to that described above in connection with struts 38.

As shown in the illustrated embodiment and similar to that described above in connection with prosthesis 10, a portion of the frame 420, such as a first or upper row of cells 436a, can extend radially outward from the longitudinal axis of the frame 420. In this manner, the cells 436a can create a flared or shoulder portion 428 of the frame 420. This flared or shoulder portion 428 can form part of the first anchoring feature 432 of the prosthesis 410. As shown in the illustrated embodiment, a portion of the frame 420, such as the cells 436a, can extend radially outward via a bend beginning at or proximate the ends the struts forming the longitudinally extending sides of the cells 436a. As shown, the cells 436a include a first bend 441a in which the cells 436a extend generally perpendicular to the longitudinal axis of the frame 420 and a second bend 441b in which the cells 436a extend upwardly. The second bend 441b can be positioned closer to the first end 422 of the frame 420 than the first bend 441a is positioned. The radius of curvature of one or both bends 441a, 441b can be relatively constant throughout the length of the bend or can differ along the length of one or both bends. For example, the radius of curvature may increase from the beginning of one or both bends 441a, 441b towards the end of one or both bends 441a, 441b or may decrease from the beginning of one or both bends 441a, 441b towards the ends of one or both bends 441a, 441b. Although two bends 441a, 441b are shown in the illustrated embodiment, a greater number of bends may also be incorporated.

As shown in the illustrated embodiment, the ends 439a of cells 436a extend in a direction which forms an acute angle relative to a perpendicular line passing through the longitudinal axis of the frame 420. For example, the angle can be between about 0 degrees and about 75 degrees, between about 10 degrees and about 60 degrees, between about 20 degrees and about 45 degrees, any sub-range within these ranges, or any other angle as desired. In other embodiments, the ends 439a of cells 436a can extend in a direction which forms an obtuse angle relative to a perpendicular line passing through the longitudinal axis of the frame 420. The ends 439a of cells 436a can be at or proximate the uppermost portion of the frame 420.

In some embodiments, the first bend 441a formed along a portion of the frame 420, such as cells 436a, can generally form an arc with an angle between about 45 degrees to about 135 degrees such that, at the end of the first bend 441a, the frame 420 extends in a direction radially outward from a longitudinal axis of the frame 420 and can extend in a direction towards the first end 422 of the frame 420, a direction perpendicular to a longitudinal axis of the frame, or a direction towards the second end 424 of the frame 420. For example, as shown in the illustrated embodiment, the arc can have an angle of about 90 degrees. In some embodiments, the first bend 441a of cells 436a can form an arc with an angle between about 0 degrees to about 90 degrees such that, at the end of the first bend 441a, the frame 420 extends in a direction radially outward from a longitudinal axis of the frame 420 and upwards.

As noted above, the radius of curvature of the arc may be constant such that the first bend 441a and/or second bend 441b forms a circular arc or may differ along the length of the first bend 441a and/or second bend 441b. In some embodiments, the frame 420 can include a first bend 441a forming an arc with an angle between about 60 degrees to about 100 degrees and a second bend 441b, in an opposite direction, which forms an arc with an angle between about 30 degrees to about 60 degrees.

With continued reference to the embodiment of FIGS. 15 and 16, as noted above, first anchoring feature 432 can include a flared or shoulder portion 428 of the frame 420 and can include ends 439a of cells 436a. Ends 439a of cells 436a can form a plurality of anchors in the form of free apices which can be used to facilitate anchoring or stabilization of the frame 420 within the body cavity. The first anchoring feature 432 can also include one or more elongate tips 433. The elongate tips 433 can extend from ends 439a of one or more cells 436a forming part of the anchoring feature 432. The second anchoring feature 434 can include one or more individual anchors, such as anchors 435a, 490a, having tips or ends, such as tips or ends 435b, 490b.

As shown in the illustrated embodiment, each of the anchoring features 432, 434 can be positioned or extend generally radially outwardly from an outer surface of the frame 420, such as the middle portion 426 so that the ends 439a of cells 436a, elongate tips 433, tips or ends 435b of anchors 435a, and tips or ends 490b of anchors 490a are generally spaced away or radially outward from the rest of the frame 420. The anchors 435a can include a base 435c located on a side opposite the tips or ends 435b. The base 435c can be for example where the anchors 435a begins to extend from or away from a second or bottom row of cells 436b. As shown in the illustrated embodiment, the anchors 435a can extend distally away from the frame at base 435c. The anchors 490a can include a base 490c located on a side opposite the tips or ends 490b. The base 490c can be for example where the anchors 490a begin to extend from or away struts 438. The dimensions of some or all of the anchors of the first anchoring feature 432, such as ends 439a and/or elongate tips 433, and/or all of the anchors of the second anchoring feature 434, such as anchors 435a, 490a can be similar to that described above in connection with first anchoring feature 32 and second anchoring feature 34.

The anchors forming the anchoring features 432, 434 can comprise first, second, third, or more spaced apart bending stages along the length of each anchor. For example, as described above, the first anchoring feature 432 can include a flared or shoulder portion 428 which has a first bend 441a and a second bend 441b. As shown in the illustrated embodiment, the anchors 435a can extend downwardly from the frame 420 in a direction generally parallel to a longitudinal axis of the frame 420. The anchors 435a can include a first bending stage 435d in which the anchors 435a extend radially outward from the longitudinal axis of the frame 420 such that the anchors 435a extend perpendicular to a longitudinal axis of the frame 420. During the first bending stage 435d, the anchors 435a can continue to bend such that the anchors are oriented towards the first end 422 of the frame 420. The anchors 435*a* can include a second bending stage 435*e* in which the anchors 435*a* bend in an opposite direction radially outward from a longitudinal axis of the frame 420. The anchors 435*a* can include a third bending stage 435*f* in which the anchors 435*a* bend in an opposite direction from the second bending stage 435*e*. During the third bending stage 435*a*, the anchors 435*a* can extend generally proximally towards the first end 422 of the frame 420 in a direction generally parallel with the longitudinal axis of the frame 420.

In some embodiments, the anchors 435*a* may extend generally perpendicular to the longitudinal axis of the frame 420. The anchors can also extend either distally or proximally before and/or after one or more of the bending stages. A portion of the anchor may extend with the frame before or after any bending stages. As shown, the anchors 435*a* can include loops as described above, having a curved or arcuate atraumatic tip to minimize damage to body tissue. Ends of the first anchoring feature 432 can also comprise loops. Anchors 490*a* can include similar structural features to those of anchors 435*a* such as the three bending stages. As shown in the illustrated embodiment, the anchors 490*a* can include a straight segment between the first bending stage in which the anchors 490*a* extend radially outward from a longitudinal axis of the frame 420 and the second bending stage in which the anchor 490*a* bends in an opposite direction from the first bending stage. The straight segment can be generally parallel with the longitudinal axis of the frame 420. It is contemplated that the straight segment can be at an acute angle relative to the longitudinal axis of the frame 420 and may extend radially outward from the frame between the first and second bending stages.

It is contemplated that fewer or greater numbers of bending stages can be used for one or both anchors 435*a*, 490*a*. As shown in the illustrated embodiment, the ends 435*b*, 490*b* of anchors 435*a*, 490*a* are generally aligned in the axial direction such that ends 435*b*, 490*b* of anchors 435*a*, 490*a* are at the same axial location relative to the outer surface of the frame 420. This can be beneficial as it can allow both anchors 435*a*, 490*a* to more easily contact the tissue, such as the native mitral valve annulus. As shown, some anchors, such as anchors 490*a*, can extend further distally than other anchors, such as anchors 435*a*.

During delivery, the anchors 435*a* (along with the frame 420) can be moved toward the ventricular side of an annulus with the anchors 435*a* extending between at least some of the chordae tendineae to provide tension on the chordae tendineae. For example, similar to the situation illustrated in FIGS. 7A, 7B and 8, a proximal portion of the anchors 435*a* can apply tension to the chordae tendineae. The degree of tension provided on the chordae tendineae can differ. In some situations, little to no tension may be present in the chordae tendineae similar to the situation illustrated in FIG. 7C. A greater degree of tension may be present in the chordae tendineae similar to the situation illustrated in FIGS. 7A, 7B and 8. In some situations, the further distal positioning of certain of the anchors, such as anchors 490*a*, can impart a lower degree of tension to the chordae tendineae. This can be particularly beneficial in situations where a patient's chordae tendineae are already subject to a greater degree of tension prior to deployment of the prosthesis 410 within the mitral annulus. Such tension can be due to factors such as an enlarged annulus.

In some situations, the prosthesis 410 can be positioned such that ends or tips 435*b* of the anchors 435*a* contact the annulus similar to the situation shown in FIGS. 7A-7C. In some situations, the prosthesis 410 can be positioned such that ends or tips 435*b* of the anchors 435*a* do not contact the annulus similar to the situation shown in FIG. 8A. In some situations, similar to those illustrated in FIGS. 7A-7C and 8, a leaflet of the native valve can be positioned between one or more of the anchors 435*a* and a portion of the frame 420 and/or the anchors 435*a*. In some situations, the prosthesis 410 can be positioned such that the portions of the second anchoring feature 434, such as one or more anchors 435*b*, do not extend around a leaflet similar to the situation shown in FIG. 9.

With continued reference to the embodiment of FIGS. 15 and 16, the elongate tips 433 can extend from an end 439*a* of the cells 436*a*. The elongate tips 433 can be curved and follow the general curvature of the cell 436*a*. For example, as shown in the illustrated embodiment, the elongate tips 433 continue the curve of the cells 436*a* and extend generally upwardly. In some embodiments, the elongate tips 433 can follow the general shape of the wall of the left atrium. The radius of curvature of the elongate tips 433 can be relatively constant throughout the length of the tip 433 or can differ along the length of the tip 433. For example, as shown in the illustrated embodiment, the radius increases towards the end of the tip 433 such that the end of tip 433 includes a generally straight segment extending upwardly.

As shown in the illustrated embodiment, the elongate tips 433 can extend generally parallel to the longitudinal axis of the frame 420. In some embodiments, the elongate tips 433 can extend in a direction which forms an acute angle relative to the longitudinal axis of the frame 420. For example, the angle can be between about 0 degrees and about 60 degrees, between about 15 degrees and about 50 degrees, between about 30 degrees and about 45 degrees, any sub-range within these ranges, or any other angle as desired.

As shown in the illustrated embodiment, the prosthesis 410 can have a first anchoring feature 432 with nine anchors, a second anchoring feature 434 with six anchors 435*a* extending from bottom apices of a bottom row of cells 436*b*, and three struts 438 having eyelets positioned between every two anchors 435*a* and three anchors 490*a* each extending from a bottom end of the struts 438. Any number of anchors can be included in first and second anchoring features 432, 434. In other embodiments, instead of a 3:2 correspondence between anchors, other ratios, such as a 1:1 or a 3:1 correspondence between the anchors, are possible. In some embodiments, the struts 438 having eyelets can be positioned between every other anchor 435*a*. In some embodiments, an anchor 490*a* can extend from each strut 438. It is contemplated that anchors 490*a* can extend from fewer than all struts 438 such that there are fewer anchors 490*a* than struts 438. Moreover, such struts 438 can be positioned between anchors of the first anchoring feature 432.

Figure 17:
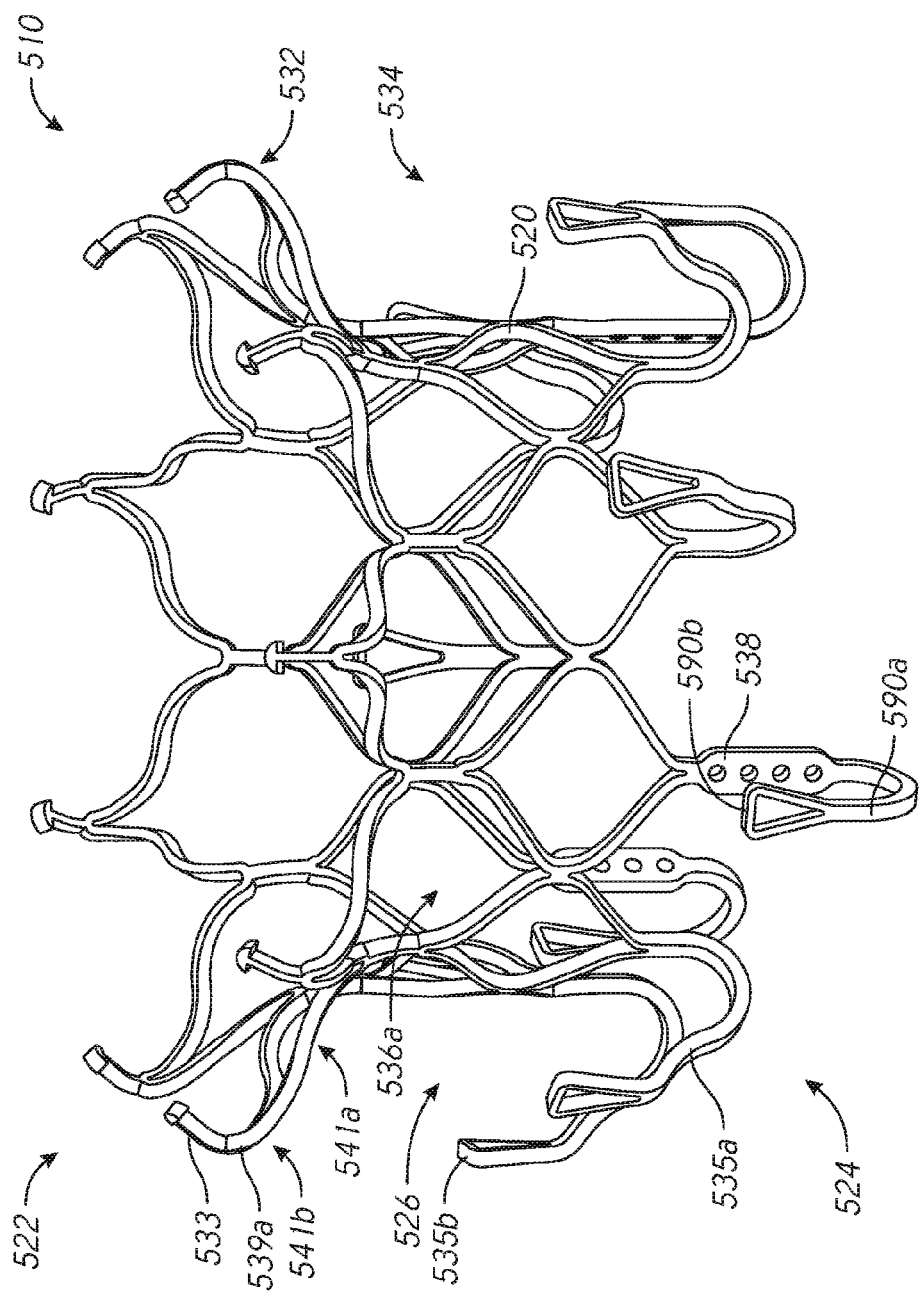
FIG. 17 is a perspective view of another embodiment of a prosthesis.

With reference next to the embodiment of FIG. 17, the prosthesis 510 can have a similar construction to prostheses 10, 210, 310, 410. Prosthesis 510 can include a frame 520, the frame 520 having a first end 522, a second end 524, a middle or intermediate portion 526, a first anchoring feature 532 and a second anchoring feature 534. Similar to prostheses 10, 210, 310, 410 one or both anchoring features 532, 534 can contact or engage a native valve annulus, such as the native mitral valve annulus, tissue beyond the native valve annulus, native leaflets, and/or other tissue at or around the implantation location. While the anchoring features 532, 534 have been illustrated as extending from the first and second ends 522, 524 of the frame 520 respectively, it should be understood that the anchoring features 532, 534 can be positioned along any other portion of the frame 520 as desired. Moreover, while two anchoring features 532, 534 have been included in the illustrated embodiment, it is contemplated that fewer or greater sets of anchoring features can be utilized.

As shown in the illustrated embodiment, a portion of the frame 520, such as the cells 536a, can extend radially outward via a bend beginning at or proximate the ends the struts forming the longitudinally extending sides of the cells 536a. As shown, the cells 536a include a first bend 541a in which the cells 536a extend generally perpendicular to the longitudinal axis of the frame 520 and a second bend 541b in which the cells 536a extend upwardly away from a second end 524 of the frame 520. During the second bend 541b, the cells 536a may bend such that they extend radially inward towards the longitudinal axis. The radius of curvature of one or both bends 541a, 541b can be relatively constant throughout the length of one or both bends 541a, 541b or can differ along the length of one or both bends 541a, 541b. For example, the radius of curvature may increase from the beginning of one or both bends 541a, 541b towards the end of one or both bends 541a, 541b or may decrease from the beginning of one or both bends 541a, 541b towards the ends of one or both bends 541a, 541b. Although two bends 541a, 541b are shown in the illustrated embodiment, a greater number of bends may also be incorporated.

As shown in the illustrated embodiment, the ends 539a of cells 536a extend in a direction which forms an obtuse angle relative to a perpendicular line passing through the longitudinal axis of the frame 520. For example, the angle can be between about 90 degrees and about 180 degrees, between about 95 degrees and about 160 degrees, between about 100 degrees and about 140 degrees, any sub-range within these ranges, or any other angle as desired. The ends 539a of cells 536a can be at or proximate the upper-most portion of the frame 520.

In some embodiments, the first bend 541a formed along a portion of the frame 520, such as cells 536a, can generally form an arc with an angle between about 45 degrees to about 135 degrees such that, at the end of the first bend 541a, the frame 520 extends in a direction radially outward from a longitudinal axis of the frame 520 and towards the second end 524 of the frame 520. For example, as shown in the illustrated embodiment, the arc can have an angle of about 90 degrees. In some embodiments, the first bend of cells 536a can form an arc with an angle between about 0 degrees to about 90 degrees such that, at the end of the bend, the frame 520 extends in a direction radially outward from a longitudinal axis of the frame 520 and upwards.

As noted above, the radius of curvature of the arc may be constant such that the first bend 541a and/or second bend 541b forms a circular arc or may differ along the length of the first bend and/or second bend 541b. In some embodiments, the frame 520 can include a first bend 541a forming an arc with an angle between about 60 degrees to about 100 degrees and a second bend 541b, in an opposite direction, which forms an arc with an angle between about 90 degrees to about 135 degrees. The radially inward bend of the frame 520 can be beneficial in orienting the ends 539a of the cells 536a and the elongate tips 533 away from walls of the heart in which the prosthesis 510 may be positioned. As shown in the illustrated embodiment, the elongate tips 533 can extend radially inwardly towards the longitudinal axis of the frame 520.

With continued reference to the embodiment of FIG. 17, the elongate tips 533 can extend from an end 539a of the cells 536a. The elongate tips 533 can be curved and follow the general curvature of the cell 536a. For example, as shown in the illustrated embodiment, the elongate tips 533 continue the curve of the cells 536a and extend generally radially inwardly towards the longitudinal axis of the frame 520. The radius of curvature of the elongate tips 533 can be relatively constant throughout the length of the tip 533 or can differ along the length of the tip 533. In some embodiments, the elongate tips 533 can be generally straight.

As shown in the illustrated embodiment, the elongate tips 533 can extend generally radially inward towards the longitudinal axis of the frame 520. In some embodiments, the elongate tips 533 can extend in a direction which forms an angle relative to the longitudinal axis of the frame 420. For example, the angle can be between about 0 degrees and about 70 degrees, between about 10 degrees and about 65 degrees, between about 20 degrees and about 60 degrees, any sub-range within these ranges, or any other angle as desired.

Second anchoring feature 534 can include anchors 535a which can share similar features to the anchors described above, such as anchors 435a. Second anchoring feature 534 can include anchors 590a which can extend from a bottom end of the struts 538 having eyelets. As shown in the illustrated embodiment, anchors 590a can extend distally from the frame 520 and include a single bending stage in which the anchor 590a extends radially outward from the longitudinal axis of the frame. During this bending stage, the anchors 590a can continue to bend such that the anchors are oriented towards the first end 522 of the frame 520. As shown in the illustrated embodiment, the anchors 490a can include a straight segment after the bending stage. The straight segment can be generally parallel with the longitudinal axis of the frame 420. It is contemplated that the straight segment can be at an acute angle relative to the longitudinal axis of the frame 420 and may extend radially outward from the frame between after the bending stage. In some embodiments, the ends 590b of anchors 590a may not be aligned with ends 535b of anchors 535a. For example, the ends 590b may be positioned distal relative to ends 535b.

Figure 18:
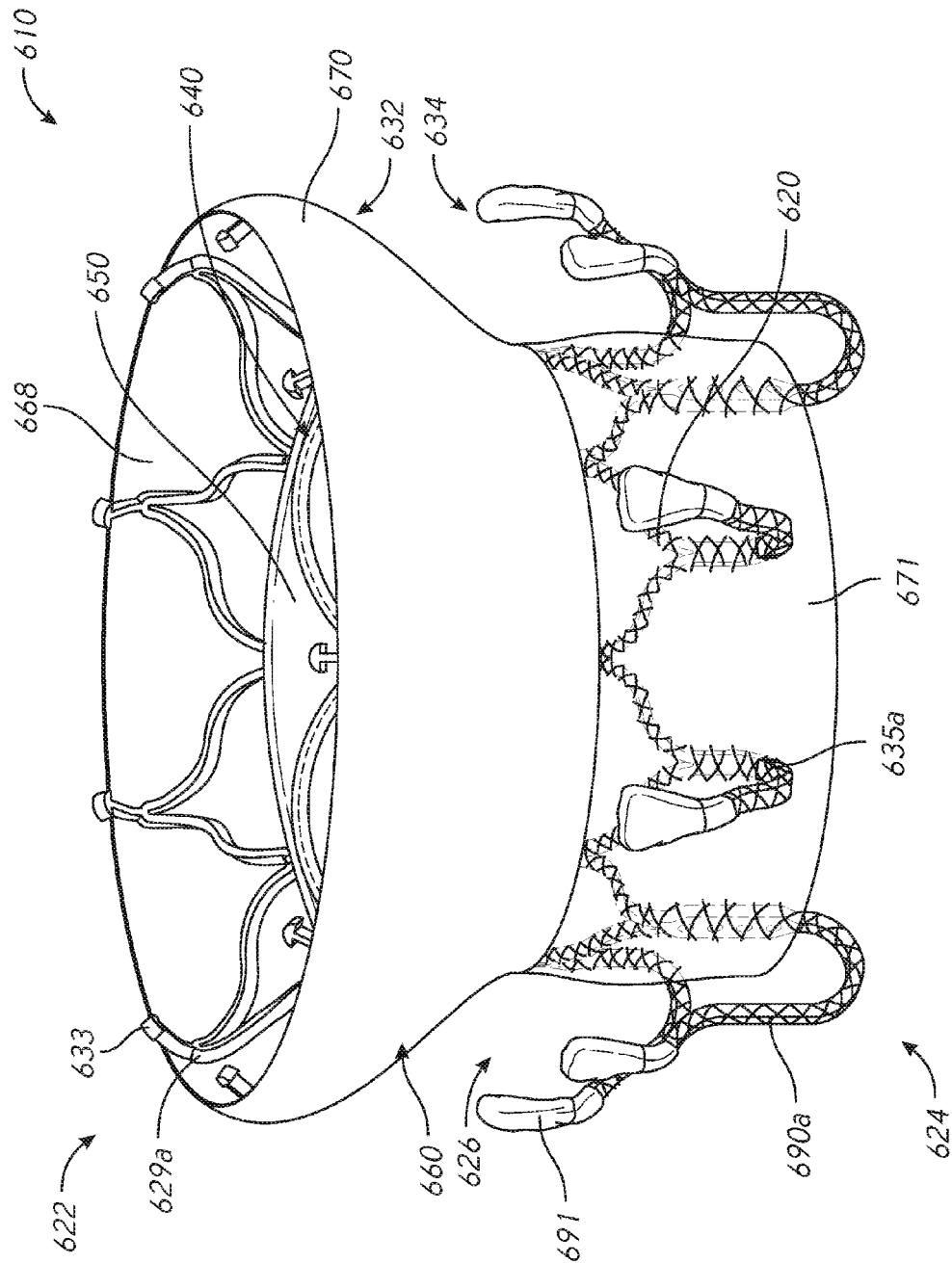
FIG. 18 is a perspective view of another embodiment of a prosthesis.
Figure 20:
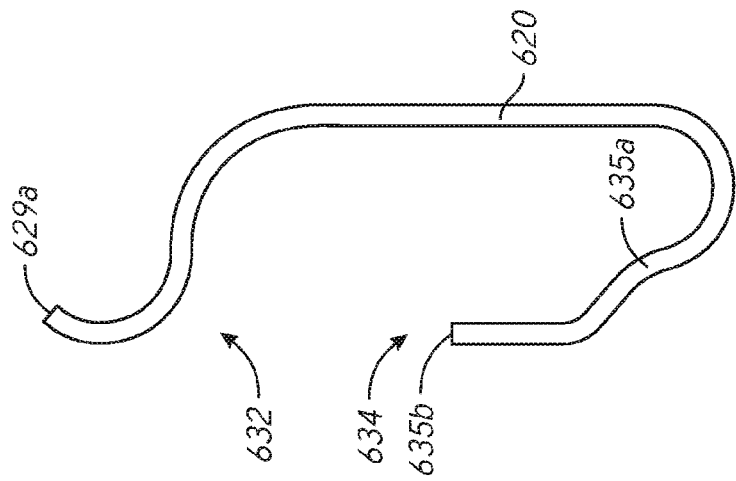
FIG. 20 illustrates a schematic representation of another side of the prosthesis of FIG. 18.
Figure 19:
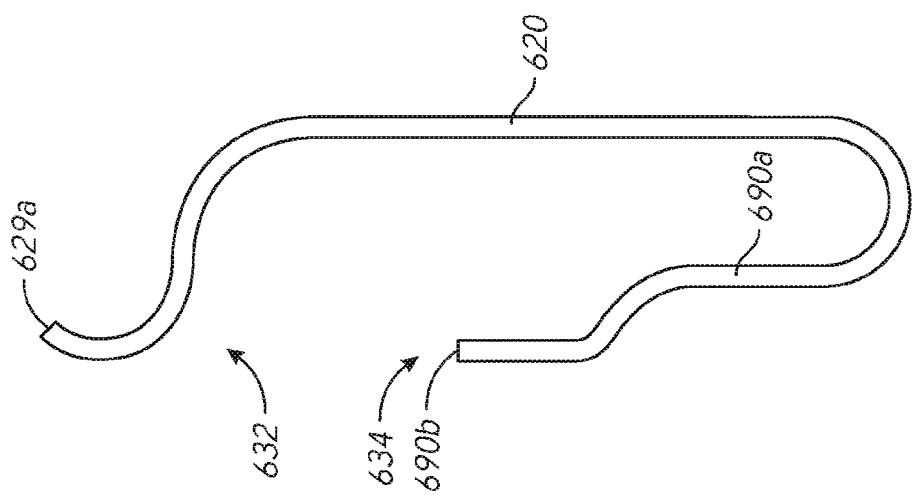
FIG. 19 illustrates a schematic representation of a side of the prosthesis of FIG. 18.

With reference next to the embodiment of FIGS. 18-20, the prosthesis 610 can have a similar construction to prostheses 10, 210, 310, 410, 510. Prosthesis 610 can include a frame 620, the frame 620 having a first end 622, a second end 624, a middle or intermediate portion 626, a first anchoring feature 632 and a second anchoring feature 634. Similar to prostheses 10, 210, 310, 410, 510 one or both anchoring features 632, 634 can contact or engage a native valve annulus, such as the native mitral valve annulus, tissue beyond the native valve annulus, native leaflets, and/or other tissue at or around the implantation location. While the anchoring features 632, 634 have been illustrated as extending from the first and second ends 622, 624 of the frame 620 respectively, it should be understood that the anchoring features 632, 634 can be positioned along any other portion of the frame 620 as desired. Moreover, while two anchoring features 632, 634 have been included in the illustrated embodiment, it is contemplated that fewer or greater sets of anchoring features can be utilized.

As shown in the illustrated embodiment, the first anchoring feature 632 can be similar to the first anchoring feature 532 of prosthesis 510. A portion of the frame 620 can extend radially outward via a first bend and a second bend in which a portion of the frame 620 extends upwardly away from a second end 624 of the frame 620 towards the longitudinal axis. Elongate tips 633 can extend from an end 639a of the portion of the frame 620. During the second bend, the cells 536a may bend such that they extend radially inward towards the longitudinal axis.

The second anchoring feature 634 can be similar to the second anchoring feature 434 of prosthesis 410. For example, anchors 635a can be similar to anchors 435a and/or anchors 690a can be similar to anchors 490a. As shown in the illustrated embodiment, the ends 635b, 690b of anchors 635a, 690a are generally aligned in the axial direction such that ends 635b, 690b of anchors 635a, 690a are at the same axial location relative to the outer surface of the frame 620. This can be beneficial as it can allow both anchors 635a, 690a to more easily contact the tissue, such as the native mitral valve annulus.

With continued reference to the embodiments of FIGS. 18-20, the prosthesis 610 can include a valve 640, liner 650, and/or flap or sail assembly 660. Valve 640, liner 650, and/or flap or sail assembly 660 can include similar components, features, and/or functionality to valve 40, liner 50, and/or flap or sail assembly 60 discussed above in connection with prosthesis 10. For example, as shown in the illustrated embodiment, the flap assembly 660 can include a first portion 668 which can extend radially outward from the frame 620 and can extend along an exterior portion of the frame 620. The flap assembly 660 can include a second portion 70 which can extend from the first portion 668 and can extend towards an opposing end of the frame 620.

As shown in the illustrated embodiment, the flap or sail assembly 660 can include a third portion 671 which extends distally along a lower portion of the frame 620. For example, in some embodiments, the third portion 671 can extend from an end of the second portion 670 and can extend distally along the frame 620. The third portion 671 can extend along an interior of the frame 620, an exterior of the frame 620, or both. The third portion 671 can beneficially gather and direct blood towards the interior of the flap assembly 660 to expand the flap assembly 660 during systole.

As shown in the illustrated embodiment, the prosthesis 610 can include one or more coverings or cushions 691 on the second anchoring feature 634 such as the ends 635b, 690b of anchors 635a, 690a. Coverings or cushions 691 can be positioned on one or more anchors of the first anchoring feature 632.

Figure 21:
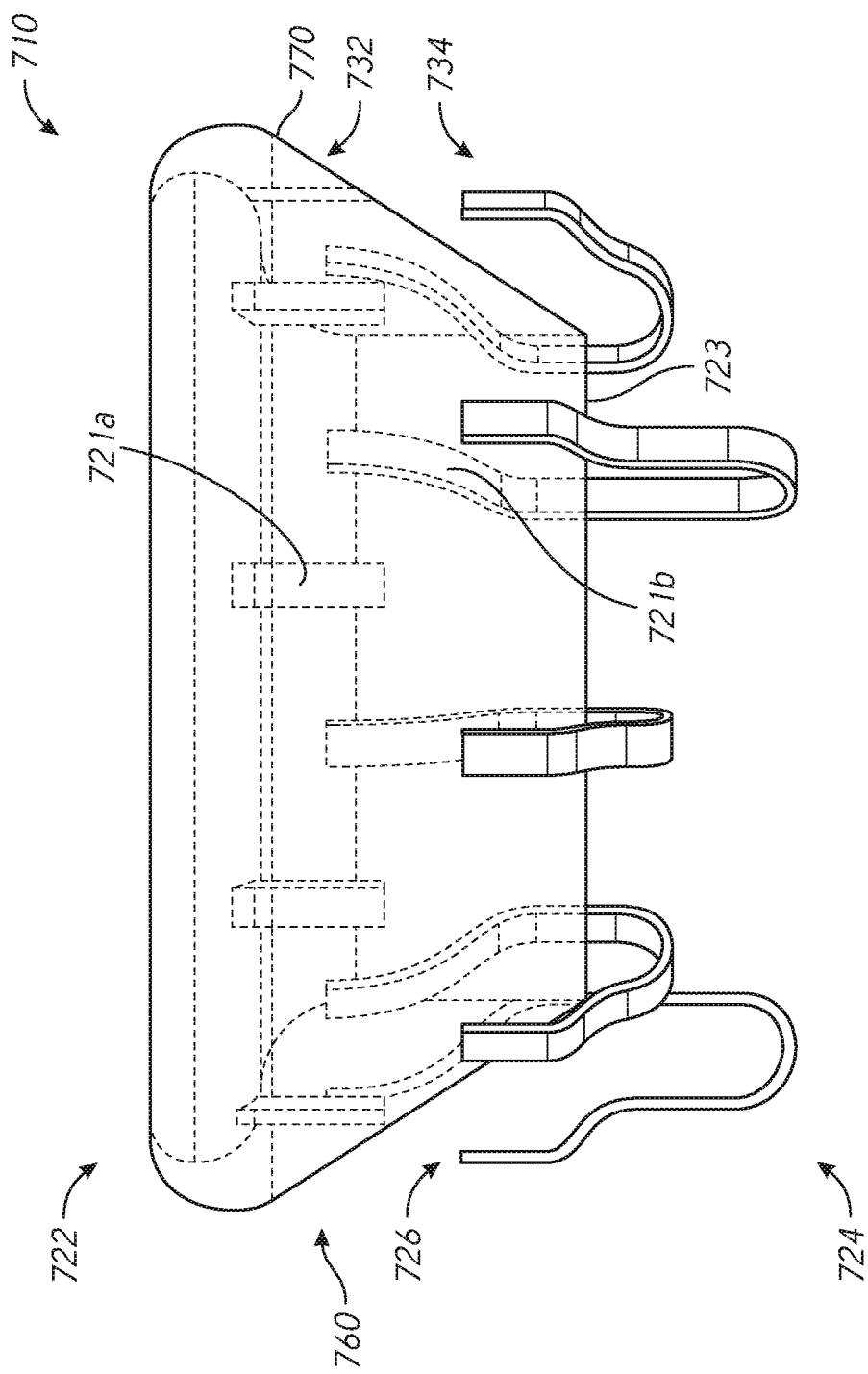
FIG. 21 is a side view of another embodiment of a prosthesis.

With reference next to the embodiment of FIG. 21, the prosthesis 710 can have a similar construction to prostheses 10, 210, 310, 410, 510, 610. Prosthesis 710 can include a frame having a first end 722, a second end 724, a middle or intermediate portion 726, a first anchoring feature 732 and a second anchoring feature 734. In the illustrated embodiment, portions of the frame, such as a cylindrical portion and portions of the first anchoring portion 732 are represented schematically as structure 723. Similar to prostheses 10, 210, 310, 410, 510, 610 one or both anchoring features 732, 734 can contact or engage a native valve annulus, such as the native mitral valve annulus, tissue beyond the native valve annulus, native leaflets, and/or other tissue at or around the implantation location. While the anchoring features 732, 734 have been illustrated as extending from the first and second ends 722, 724 of the frame respectively, it should be understood that the anchoring features 732, 734 can be positioned along any other portion of the frame as desired. Moreover, while two anchoring features 732, 734 have been included in the illustrated embodiment, it is contemplated that fewer or greater sets of anchoring features can be utilized.

The prosthesis 710 can include a flap assembly 760 which can include a portion 770 similar to second portion 70 which can extend radially outward from the frame. As shown in the illustrated embodiment and similar to the embodiments of prostheses 210, 310, the prosthesis 710 can include arms 721a and/or 721b which extend from portions of the frame. Arms 721a can extend distally from a portion of the frame and can extend generally parallel to a longitudinal axis of the frame when the frame is in an expanded configuration. It is contemplated that the arms 721a can extend in a direction which is not parallel to a longitudinal axis of the frame. For example, the arms 721a can extend in a direction radially inward towards a longitudinal axis of the frame or in a direction radially outward from the longitudinal axis. Arms 721b can extend radially outward from the longitudinal axis of the frame when the frame is in an expanded configuration. As shown in the illustrated embodiment, the arms 721b can extend from the frame in a direction towards the first end 722 of the frame. The arms 721a, 721b can contact a flap assembly, such as flap assembly 760, to bias the flap assembly towards an inflated or expanded configuration even in the absence of fluid within the flap assembly. For example, the arms 721a, 721b can support the flap assembly 760 and reduce the likelihood of deflation or collapse during the diastolic cycle.

Figure 22:
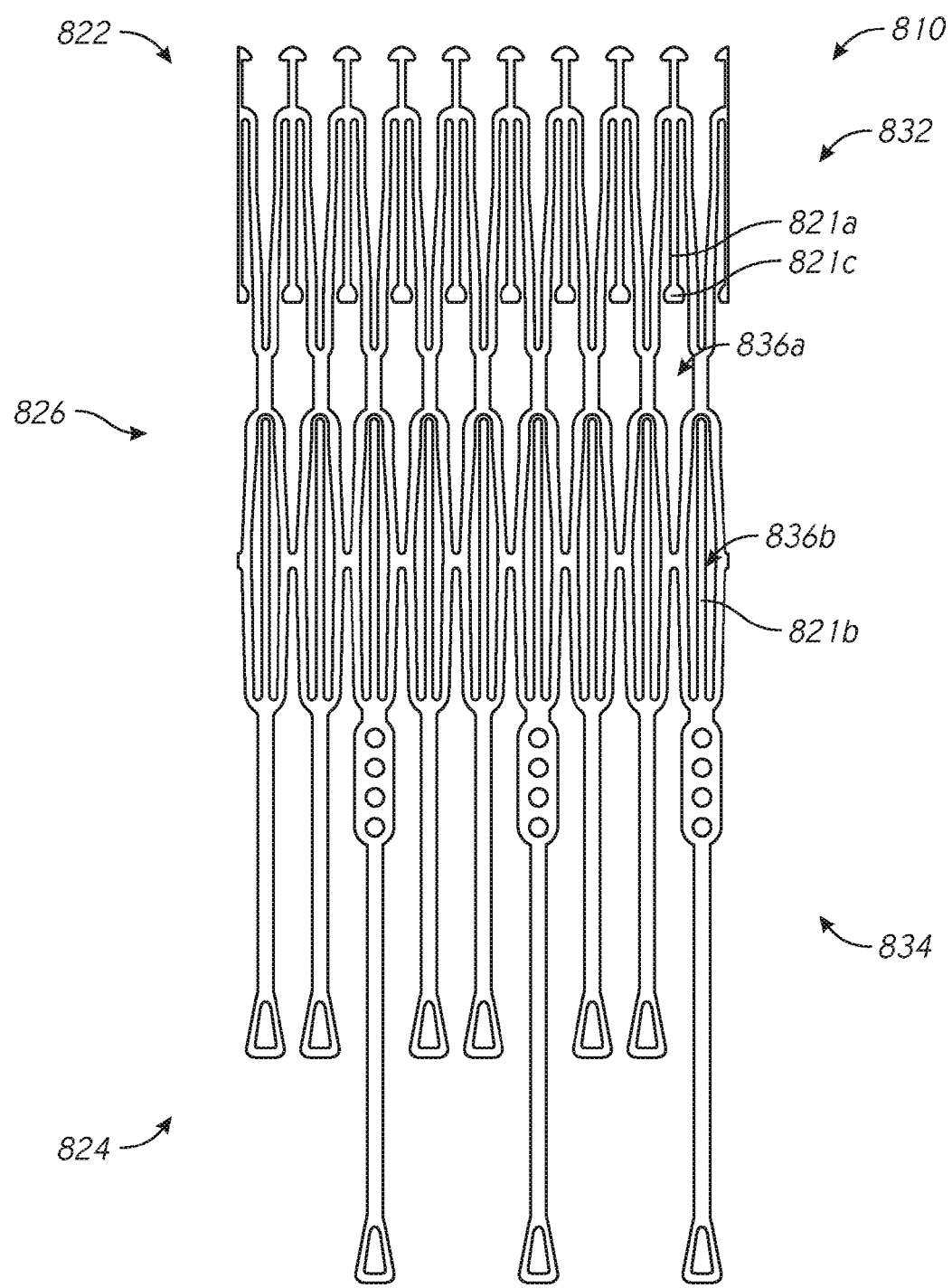
FIG. 22 is a flat pattern for another embodiment of a prosthesis.

With reference next to the embodiment of FIG. 22, a flat pattern for the prosthesis 810 is shown. The prosthesis 810 can have a similar construction to prostheses 10, 210, 310, 410, 510, 610, 710. Prosthesis 810 can include a frame 820 having a first end 822, a second end 824, a middle or intermediate portion 826, a first anchoring feature 832 and a second anchoring feature 834. Similar to prostheses 10, 210, 310, 410, 510, 610, 710 one or both anchoring features 832, 834 can contact or engage a native valve annulus, such as the native mitral valve annulus, tissue beyond the native valve annulus, native leaflets, and/or other tissue at or around the implantation location. While the anchoring features 832, 834 have been illustrated as extending from the first and second ends 822, 824 of the frame respectively, it should be understood that the anchoring features 832, 834 can be positioned along any other portion of the frame as desired. Moreover, while two anchoring features 832, 834 have been included in the illustrated embodiment, it is contemplated that fewer or greater sets of anchoring features can be utilized.

The first anchoring feature 832 can be similar to the first anchoring features described herein. As shown in the illustrated embodiment, one or more arms 821a can extend from interior portions of cells 836a. For example, the arms 821a can extend from an upper or proximal apex of the cells 836a and extend towards the second end 824 of the frame 820. The arms 821a can be similar to arms 721a. One or more arms 821b can extend from interior portions of cells 836b. The arms 821b can extend from a lower or distal apex of cells 836b and extend towards the first end 822 of the frame 820. The arms 821b can be similar to arms 721b. The arms 821a, 821b can contact a flap assembly, such as flap assembly 760, to bias the flap assembly towards an inflated or expanded configuration even in the absence of fluid within the flap assembly. As shown in the illustrated embodiment, the arm 821a can include an enlarged head 821c. The enlarged head 821c and can be configured to reduce the likelihood of puncturing the flap assembly.

Figure 23:
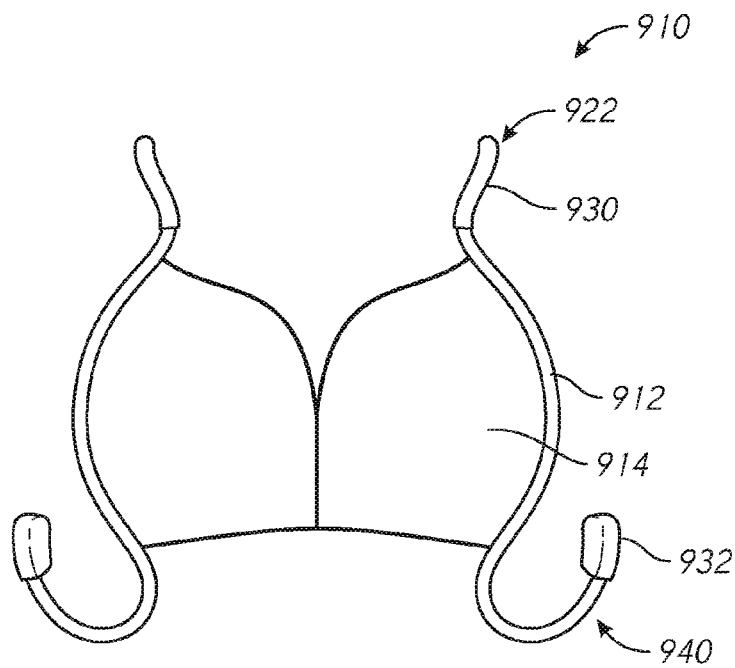
FIG. 23 is a schematic representation of an embodiment of a prosthesis with bio-resorbable components.

With reference next to the embodiment of FIG. 23, the prosthesis 910 can be formed from a metal structure 912, such as Nitinol, and include one or more bioresorbable components. The prosthesis can include a valve 914. As shown in the illustrated embodiment, the prosthesis 910 can include one or more bio-resorbable components 930 at or proximate a first end 922 of the prosthesis 910. The bio-resorbable components 930 can be used, for example, with a delivery system. In some embodiments, the bio-resorbable components 930 can include tips, similar to tips 33, and/or eyelets which can engage a locking mechanism of a delivery system. Use of bio-resorbable components 930 to form portions of the prosthesis 910 intended to engage a delivery system can be particularly beneficial as such portions may serve little to no function after the prosthesis 910 is implanted within the patient. As such, removal of such features advantageously reduce the overall size of the prosthesis 910 after implantation. In some embodiments, the bio-resorbable components 930 can be chosen such that they are absorbed within the body shortly after implantation. For example, the bio-resorbable components 930 can be chosen such that they are absorbed within a couple of hours to a week after implantation.

The prosthesis 910 can include one or more bio-resorbable components 932 at or proximate tips or ends of an anchoring feature 940 of the prosthesis 910. This can beneficially be used to enhance leaflet capture during initial implantation of the prosthesis 910. Moreover, this can beneficially enhance securement of the prosthesis 910 to the native valve prior to sufficient or full tissue ingrowth. In some embodiments, the bio-resorbable components 932 can be chosen such that they are absorbed within the body after sufficient or full tissue ingrowth has occurred. For example, the bio-resorbable components 932 can be chosen such that they are absorbed within a couple of days or a couple of months.

The bio-resorbable portions 930, 932 can be formed from bio-resorbable materials such as, but not limited to, polylactic acid (PLA), polylactic-co-glycolic acid (PLGA), and/or a combination thereof. The composition can be chosen to alter the amount of time prior to full absorption. In some embodiments, the bio-resorbable portion 930 can be formed from a composition allowing for faster aborption than the bio-resorbable portion 932. The bio-resorbable portions can be locked onto the metal frame portions of the prosthesis 910 and/or can be overmolded onto the metal frame portions of the prosthesis 910.

Figure 24:
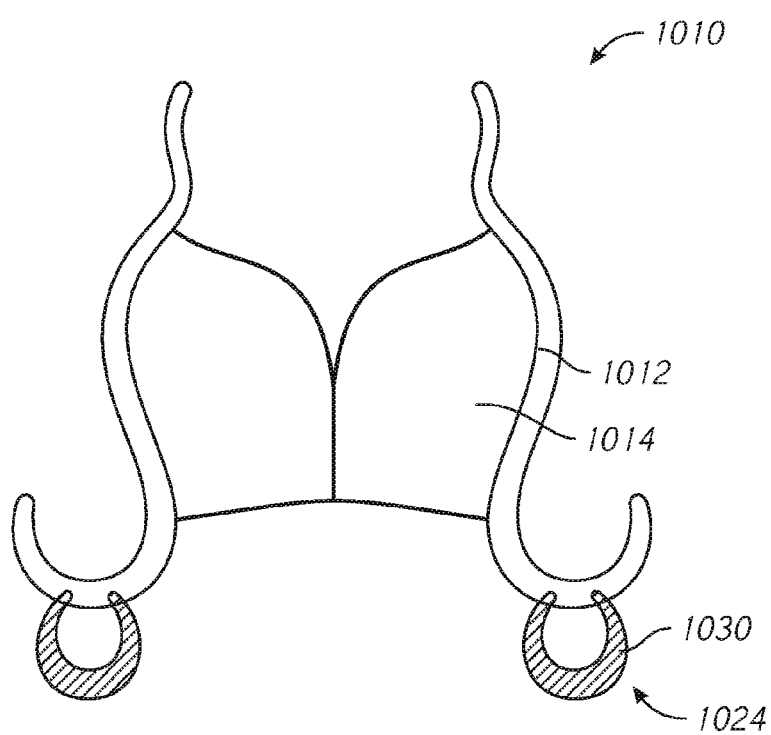
FIG. 24 is a schematic representation of another embodiment of a prosthesis with bio-resorbable components.

With reference next to the embodiment of FIG. 24, the prosthesis 1010 can be formed from a metal structure 1012, such as Nitinol, and include one or more bioresorbable components. The prosthesis can include a valve 1014. As shown in the illustrated embodiment, the prosthesis 1010 can include one or more bio-resorbable components 1030 at or proximate an end 1024 of the prosthesis 1010. As shown in the illustrated embodiment, the bio-resorbable component 1030 can form an aperture or hole 1032 between the bio-resorbable component 1030 and the metal structure of the prosthesis 1010. The bio-resorbable components 1030 can be used, for example, with a delivery system to enable recapture of the prosthesis 1010. It is to be understood that other shapes can be used. For example, in some embodiments, the bio-resorbable components 1030 can have a hook-shape.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A valve prosthesis configured to be deployed within a native heart valve at a native heart valve annulus, the valve prosthesis comprising:
    an expandable frame comprising a proximal end, a distal end, a middle portion between the proximal end and the distal end, and a longitudinal axis extending therethrough, the frame configured to collapse radially for delivery and to expand radially upon deployment;
    a plurality of circumferentially spaced apart distal anchors extending from the distal end of the frame towards the proximal end and expandable from a collapsed configuration to an expanded configuration, each of the plurality of circumferentially spaced apart distal anchors covered at least partially by a cushion;
    a plurality of tips having enlarged ends extending from the proximal end and configured to engage a locking mechanism of a delivery system for the prosthesis, wherein when the valve prosthesis is expanded at the native heart valve the plurality of tips are configured to be located on a first side of the native heart valve annulus and the plurality of circumferentially spaced apart distal anchors are configured to be located on a second side of the native heart valve annulus;
    a valve body positioned within an interior of the expandable frame, wherein the valve body comprises a plurality of leaflets configured to allow flow in a first direction and prevent flow in a second opposite direction;
    a flap assembly positioned around and secured to an exterior of the expandable frame; and
    a biasing outer portion positioned radially outward and extending circumferentially around the middle portion of the frame when the frame is in an expanded configuration, the biasing outer portion being configured to bias the flap assembly radially outward from the longitudinal axis of the frame to provide a space having a distal opening between the flap assembly and the valve body;
    wherein when fluid flows into the space, the flap assembly creates a barrier to fluid flow exterior to the middle portion of the frame when the valve prosthesis is deployed within the native heart valve.

2. The valve prosthesis of claim 1, wherein the biasing outer portion comprises a plurality of biasing arms.

3. The valve prosthesis of claim 1, wherein the biasing outer portion extends radially outward from the frame.

4. The valve prosthesis of claim 1, wherein the biasing outer portion extends towards the proximal end of the frame.

5. The valve prosthesis of claim 1, wherein the biasing outer portion extends towards the distal end of the frame.

6. The valve prosthesis of claim 1, wherein the biasing outer portion is configured to bias the flap assembly radially outward from an exterior of the middle portion of the frame.

7. The valve prosthesis of claim 1, wherein the biasing outer portion is positioned along an exterior of the flap assembly.

8. The valve prosthesis of claim 1, wherein a proximal end of the flap assembly follows a curvature of the proximal end of the frame.

9. The valve prosthesis of claim 1, wherein a proximal end of the flap assembly extends along an exterior of the proximal end of the frame.

10. The valve prosthesis of claim 1, wherein a proximal end of the flap assembly extends along an interior of the proximal end of the frame.

11. The prosthesis of claim 1, wherein the valve body comprises a liner extending along an interior of the frame.

12. The prosthesis of claim 11, wherein the liner is attached to the leaflets of the valve body.

13. The prosthesis of claim 11, wherein the flap assembly is attached to the liner.

14. The prosthesis of claim 1, further comprising a proximal anchoring feature extending from the frame and expandable from a collapsed configuration to an expanded configuration.

15. The prosthesis of claim 1, further comprising one or more bio-resorbable components.

16. The prosthesis of claim 15, wherein at least one of the one or more bio-resorbable components is configured to engage a delivery system.

17. The prosthesis of claim 15, wherein at least one of the one or more bio-resorbable components is configured to be positioned at or proximate tips of the distal anchoring feature.

18. A valve prosthesis configured to be deployed within a native heart valve, the valve prosthesis comprising:
    an expandable frame comprising a proximal end, a distal end and a longitudinal axis extending therethrough, the frame configured to collapse radially for delivery and to expand radially upon deployment;
    a distal anchoring feature extending from the frame and expandable from a collapsed configuration to an expanded configuration;
    a valve body positioned within an interior of the expandable frame, wherein the valve body comprises a plurality of leaflets configured to allow flow in a first direction and prevent flow in a second opposite direction;
    a flap assembly positioned around and secured to an exterior of the expandable frame;
    a first biasing assembly, the first biasing assembly comprising at least one first biasing arm extending radially outward from the frame and towards the proximal end when the frame is in an expanded configuration, the at least one first biasing arm being configured to bias the flap assembly radially outward from the longitudinal axis of the frame to provide a space between the flap assembly and the valve body; and
    a second biasing assembly, the second biasing assembly comprising at least one second biasing arm extending radially outward from the frame and towards the distal end when the frame is in an expanded configuration, the at least one second biasing arm being configured to bias the flap assembly radially outward from the longitudinal axis of the frame to provide a space between the flap assembly and the valve body;
    wherein fluid flow into the space causes the flap assembly to move from a first configuration to a second configuration configured to create a barrier to fluid flow exterior to the frame when the valve prosthesis is deployed within the native heart valve.

19. The prosthesis of claim 1, wherein the proximal end has a zig-zag configuration.

20. The prosthesis of claim 1, wherein each of the plurality of circumferentially spaced apart distal anchors ends at a generally triangular tip.

21. The prosthesis of claim 1, wherein the plurality of tips are inclined radially inwards towards the longitudinal axis.

22. The prosthesis of claim 1, wherein the biasing outer portion is configured to position the flap assembly on an inflow side of the native heart valve when the frame is in the expanded configuration.

23. The prosthesis of claim 1, wherein the flap assembly is located on an exterior of the expandable frame at a first portion of the expandable frame and on an interior of the expandable frame at a second portion of the expandable frame.

24. The prosthesis of claim 1, wherein the middle portion is generally cylindrical.

\* \* \* \* \*